US012752124B2

(12) United States Patent
Joshi et al.

(10) Patent No.: US 12,752,124 B2
(45) Date of Patent: Oct. 6, 2026

(54) SYSTEM AND METHOD FOR IMPLANTABLE MEDICAL DEVICE REMOTE PROGRAMMING

(71) Applicant: Pacesetter, Inc., Sylmar, CA (US)

(72) Inventors: Suneela Joshi, Stevenson Ranch, CA (US); Maobing Jin, San Jose, CA (US); Nidhi Narang, Fremont, CA (US); Voltaire Selverian, Los Angeles, CA (US); Pulkit Bisen, Valencia, CA (US); Chinsoo Kang, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 503 days.

(21) Appl. No.: 18/337,282

(22) Filed: Jun. 19, 2023

(65) Prior Publication Data

US 2023/0414951 A1 Dec. 28, 2023

Related U.S. Application Data

(60) Provisional application No. 63/380,420, filed on Oct. 21, 2022, provisional application No. 63/367,064, filed on Jun. 27, 2022.

(51) Int. Cl.

*A61N 1/372* (2006.01)
*G16H 40/67* (2018.01)

(52) U.S. Cl.

CPC ..... *A61N 1/37241* (2013.01); *A61N 1/37247* (2013.01); *A61N 1/37264* (2013.01); *A61N 1/37282* (2013.01); *G16H 40/67* (2018.01)

(58) Field of Classification Search

CPC ............ A61N 1/37241; A61N 1/37247; A61N 1/37264; A61N 1/37282; A61N 1/37235; G16H 40/67

See application file for complete search history.

(56) References Cited

U.S. PATENT DOCUMENTS

| | | | |
|---|---|---|---|
| 5,720,770 | A | 2/1998 | Nappholz et al. |
| 5,752,976 | A | 5/1998 | Duffin et al. |

(Continued)

FOREIGN PATENT DOCUMENTS

| | | |
|---|---|---|
| EP | 1478432 B1 | 7/2009 |
| EP | 3352847 A1 | 8/2018 |

(Continued)

OTHER PUBLICATIONS

Extended EP Search Report received for related EP App. No. 23178820.9 dated Oct. 23, 2023 (6 pages).

(Continued)

*Primary Examiner* — Eugene T Wu

(74) *Attorney, Agent, or Firm* — Dean D. Small; Carroll, Hoette & Butscher, LLC

(57) ABSTRACT

A medical device assembly is provided that includes a clinician programing device configured to communicate with an implanted medical device of a patient. The clinician programming device includes one or more processors configured to communicate program instructions to a remote programming engine. The remote programming engine includes one or more processors configured to simulate operation of the implanted medical device based on the updated program instructions, and communicate updated program instructions to the implanted medical device based on the operation simulated.

14 Claims, 19 Drawing Sheets

(56) References Cited

U.S. PATENT DOCUMENTS

| | | | |
|---|---|---|---|
| 6,480,745 | B2 | 11/2002 | Nelson et al. |
| 6,622,045 | B2 | 9/2003 | Snell et al. |
| 6,878,112 | B2 | 4/2005 | Linberg et al. |
| 7,060,031 | B2 | 6/2006 | Webb et al. |
| 7,181,286 | B2 | 2/2007 | Sieracki et al. |
| 7,460,910 | B2 | 12/2008 | Webb |
| 7,565,197 | B2 | 7/2009 | Haubrich et al. |
| 7,697,994 | B2 | 4/2010 | VanDanacker et al. |
| 7,983,753 | B2 | 7/2011 | Severin |
| 8,005,546 | B1 | 8/2011 | Levine |
| 8,068,917 | B2 | 11/2011 | Petersen et al. |
| 8,073,542 | B2 | 12/2011 | Doerr |
| 8,190,900 | B2 | 5/2012 | Corndorf |
| 8,239,025 | B2 | 8/2012 | Reinke |
| 8,265,757 | B2 | 9/2012 | Mass et al. |
| 8,347,365 | B2 | 1/2013 | Jelatis et al. |
| 8,352,039 | B2 | 1/2013 | Davis et al. |
| 8,417,339 | B2 | 4/2013 | Doerr et al. |
| 8,423,149 | B2 | 4/2013 | Hennig |
| 8,615,299 | B2 | 12/2013 | Goetz |
| 8,655,447 | B2 | 2/2014 | Kukla et al. |
| 8,694,115 | B2 | 4/2014 | Goetz |
| 8,725,269 | B2 | 5/2014 | Nolan et al. |
| 8,798,760 | B2 | 8/2014 | Hoyme et al. |
| 8,818,522 | B2 | 8/2014 | Mass et al. |
| 8,855,781 | B2 | 10/2014 | Doerr |
| 8,958,870 | B2 | 2/2015 | Gerber et al. |
| 8,977,360 | B2 | 3/2015 | Kim et al. |
| 9,348,974 | B2 | 5/2016 | Goetz |
| 9,401,894 | B2 | 7/2016 | Kaplin et al. |
| 9,436,481 | B2 | 9/2016 | Drew |
| 9,480,846 | B2 | 11/2016 | Strother et al. |
| 9,633,170 | B2 | 4/2017 | Goetz |
| 9,713,724 | B2 | 7/2017 | Petersen et al. |
| 9,747,431 | B2 | 8/2017 | Chow |
| 9,781,086 | B2 | 10/2017 | Jelatis et al. |
| 9,782,596 | B2 | 10/2017 | Vamos et al. |
| 9,878,166 | B2 | 1/2018 | Thacker et al. |
| 9,979,810 | B2 | 5/2018 | Mazar |
| 10,029,106 | B2 | 7/2018 | Gupta et al. |
| 10,055,550 | B2 | 8/2018 | Goetz |
| 10,124,177 | B2 | 11/2018 | Kumar |
| 10,307,600 | B2 | 6/2019 | Ney et al. |
| 10,322,287 | B2 | 6/2019 | Strother et al. |
| 10,541,977 | B2 | 1/2020 | Wu et al. |
| 10,549,105 | B2 | 2/2020 | Klimovitch et al. |
| 10,806,344 | B2 | 10/2020 | Goetz |
| 10,819,713 | B2 | 10/2020 | Marnfeldt |
| 10,967,190 | B2 | 4/2021 | Crawford |
| 11,154,717 | B2 | 10/2021 | Giftakis et al. |
| 11,164,674 | B2 | 11/2021 | Lange |
| 11,694,799 | B2 | 7/2023 | Horton et al. |
| 2005/0049656 | A1 | 3/2005 | Petersen et al. |
| 2006/0074462 | A1 | 4/2006 | Verhoef |
| 2006/0074465 | A1 | 4/2006 | Webb |
| 2006/0161214 | A1 | 7/2006 | Patel |
| 2006/0189854 | A1 | 8/2006 | Webb |
| 2009/0054948 | A1 | 2/2009 | Webb |
| 2009/0112289 | A1 | 4/2009 | Lee et al. |
| 2010/0125174 | A1 | 5/2010 | Bevan et al. |
| 2010/0228314 | A1 | 9/2010 | Goetz |
| 2010/0228322 | A1 | 9/2010 | Nolan et al. |
| 2010/0292556 | A1 | 11/2010 | Golden |
| 2011/0015693 | A1 | 1/2011 | Williamson |
| 2011/0037614 | A1 | 2/2011 | Verhoef |
| 2011/0172737 | A1 | 7/2011 | Davis et al. |
| 2011/0191828 | A1 | 8/2011 | Gould et al. |
| 2011/0257700 | A1 | 10/2011 | Levine |
| 2012/0035686 | A1 | 2/2012 | Petersen et al. |
| 2012/0197353 | A1 | 8/2012 | Donnelly et al. |
| 2013/0283030 | A1 | 10/2013 | Drew |
| 2014/0107567 | A1 | 4/2014 | Geotz |
| 2016/0253471 | A1 | 9/2016 | Volpe |
| 2016/0342762 | A1 | 11/2016 | Goetz |
| 2017/0050035 | A1 | 2/2017 | Gupta et al. |
| 2017/0120062 | A1 | 5/2017 | Kumar |
| 2017/0143983 | A1 | 5/2017 | Strother et al. |
| 2017/0157410 | A1* | 6/2017 | Moffitt .................. G16H 70/20 |
| 2018/0309766 | A1 | 10/2018 | Marnfeldt |
| 2019/0349379 | A1 | 11/2019 | Thomas |
| 2020/0162437 | A1 | 5/2020 | Lange |
| 2020/0372996 | A1* | 11/2020 | Abdeen .................. G01R 27/02 |
| 2020/0391039 | A1 | 12/2020 | Ball et al. |
| 2021/0000349 | A1 | 1/2021 | Goetz |
| 2021/0035674 | A1 | 2/2021 | Volosin et al. |
| 2021/0052900 | A1 | 2/2021 | Pepin et al. |
| 2021/0236830 | A1 | 8/2021 | Tahmasian |
| 2021/0268296 | A1 | 9/2021 | Flakne et al. |
| 2021/0343017 | A1 | 11/2021 | Jordan |
| 2022/0028566 | A1 | 1/2022 | Debates et al. |
| 2022/0096847 | A1 | 3/2022 | Shah et al. |
| 2022/0141663 | A1 | 5/2022 | Kothandaraman et al. |

FOREIGN PATENT DOCUMENTS

| | | | |
|---|---|---|---|
| EP | 3615136 | B1 | 6/2021 |
| WO | 2020092966 | A1 | 5/2020 |

OTHER PUBLICATIONS

Extended EP Search Report received for related EP App. No. 23178821.7 dated Oct. 25, 2023 (8 pages).

Office Action mailed Mar. 9, 2025 for corresponding EP Application No. 23 178 821.7 (4 pages).

* cited by examiner

SYSTEM AND METHOD FOR IMPLANTABLE MEDICAL DEVICE REMOTE PROGRAMMING

CROSS-REFERENCE TO RELATED APPLICATIONS

This application claims priority to U.S. Provisional Patent Application No. 63/367,064, filed Jun. 27, 2022, and titled System And Method For Implantable Medical Device Remote Programming, and U.S. Provisional Patent Application No. 63/380,420, filed Oct. 21, 2022, and titled System And Method For Implantable Medical Device Remote Programming. The subject matter of the provisional applications is incorporated herein by reference in their entireties.

BACKGROUND

Embodiments of the present disclosure generally relate to methods, systems, and devices for updating operating configurations of implantable medical devices (IMDs) via remote communications and providing medical care from a remote location.

An IMD is a medical device that is configured to be implanted within a patient anatomy and commonly employs one or more electrodes that either receive or deliver voltage, current or other electromagnetic pulses from or to an organ or tissue for diagnostic or therapeutic purposes. In general, IMDs include a battery, electronic circuitry, a pulse generator, a transceiver, and a microprocessor. The microprocessor is configured to handle communication with an external device or instrument as well as control patient therapy. The components of the IMD are hermetically sealed within a housing. The IMD is completely enclosed within the human body. Thus, there is no means of direct interaction between an IMD and an external device, other than through wireless communication.

As technologies advance, new ways of providing medical care for patients, including those with IMDs, are provided. With communications advances, remote health care by a clinician of a patient is becoming more common, with patients communicating with a clinician via web conferencing. In addition, remote communication, and programming of IMDs can also occur.

For example, an IMD may require programming updates over time to adjust the behavior and operations of the IMD. The programming updates are wirelessly communicated from an external device outside of the patient to the IMD within the patient. When updating the IMD, care must be taken to ensure that the software, firmware, application, program, or the like that is being updated is the software, firmware, application, program, or the like of the update. For example, when a patient experiences a health issue with their IMD and goes to a hospital, a clinician at the hospital can change a treatment, updates the software, firmware, application, program, or the like of the IMD. If the patient then goes to their regular clinician, and the regular clinician has a different treatment, or update they desire to implement, it is important to the regular clinician to know the current treatment, updates to the software, firmware, application, program, etc. before making such a change. Otherwise, mistakes can occur related to the update, potentially harming the patient.

Still, a need for greater remote control is still desired. By having remote control over an IMD, or in association with a patient, burden can be removed from field teams. Field representatives can reduce travel and expense by using remote communication and programming, freeing up these field reps for more complex cases. In addition, by having remote control of health care, including IMDs, necessary care can be provided in a timely manner without the patient having to wait for a field representative to show up at the location of the patient.

In addition, greater demand is present for remote medical care. Clinicians and clinician support representatives desire to communicate with one another to diagnosis conditions, provide treatments, and the like for a local patient while the clinician support representative is at a remote location.

In all, a need remains for improved methods and systems for administering remote communications, including programming communications to update an IMD.

SUMMARY

In accordance with an embodiment, a medical device assembly is provided that includes a clinician programing device configured to communicate with an implanted medical device of a patient. The clinician programming device includes one or more processors configured to communicate program instructions to a remote programming engine. The remote programming engine includes one or more processors configured to simulate operation of the implanted medical device based on the updated program instructions and communicate updated program instructions to the implanted medical device based on the operation simulated.

Optionally, to simulate operation of the implanted medical device, the one or more processors of the remote programming engine are further configured to determine initialization of the programming session, whether the programming session is pending, and termination of the programming session. In one aspect, the one or more processors of the remote programming engine are further configured to determine whether the termination of the programming session is in response to completion of the programming session, or in response to a programming error. Optionally, to determine initialization of the programming session, the one or more processors of the remote programming engine are further configured to generate an asynchronous remote programming profile that includes the updated program instructions and communicate the asynchronous remote programing profile to the implanted medical device. In yet another aspect, the one or more processors of the clinician processing device are further configured to generate and display a pending message in response to communication of the asynchronous remote programing profile and present the pending message until an acknowledgment message is received from a patient application. Optionally, the one or more processors of the clinician processing device are further configured to display a success message in response to receiving the acknowledgment message. Alternatively, the one or more processors of the remote programming engine are further configured to start a timer in response to communicating the asynchronous remote programing profile and communicate a failure message in response to the timer reaching a determined period before receiving the acknowledgment message.

In accordance with an embodiment, a method for updating instructions for an implanted medical device under control of one or more processors is provided. The method includes communicating updated program instructions related to a programming session of the implanted medical device, simulating operation of the implanted medical device based on the updated program instructions, and communicating the updated program instructions to the implanted medical device based on the operation simulated.

Optionally, simulating operation of the implanted medical device includes initializing an updated programming session, determining whether the updated programming session is pending, and terminating of the updated programming session. In one aspect, initializing the updated programming session includes communicating an update message to a virtual device engine (VDE), the message including the updated program instructions for the updated programming session that is related to a treatment to be performed by the implanted medical device, accessing a patient profile in response to receiving the update message at the virtual device engine, generating an asynchronous remote programming profile that includes the updated program instructions, and communicating the asynchronous remote programing profile to the implanted medical device. In yet another aspect, the method also includes generating and displaying a pending message in response to communicating the asynchronous remote programing profile and presenting the pending message until an acknowledgment message is received from a patient application. In one example, the method also includes displaying a success message in response to receiving the acknowledgment message. In another example, the method also includes starting a timer in response to communicating the asynchronous remote programing profile and displaying a failure message in response to the timer reaching a determined period before receiving the acknowledgment message. In yet another example, the method additionally includes logging operation of programming sessions within a virtual device engine database in response to the timer reaching the determine period before receiving the acknowledgment message.

In an example embodiment a computer program product comprising a non-signal computer readable storage medium is provided, including computer executable code to obtain updated program instructions related to a programming session of an implanted medical device, simulate operation of the implanted medical device based on the updated program instructions, and communicate the updated program instructions to the implanted medical device based on the operation simulated.

Optionally, to simulate operation of the implanted medical device, the computer executable code to determine initialization of the programming session, whether the programming session is pending, and termination of the programming session. In one aspect, computer executable code to additionally determine whether the termination of the programming session is in response to completion of the programming session, or in response to a programming error. In another aspect, to determine initialization of the programming session, the computer executable code also to access a patient profile at a virtual device engine (VDE) in response to obtaining the updated program instructions, generate an asynchronous remote programming profile that includes the updated program instructions, and communicate the asynchronous remote programing profile to the implanted medical device. In one example, the computer executable code additionally to generate a pending message in response to communicating the asynchronous remote programing profile and present the pending message until an acknowledgment message is received from a patient application. In another example, the computer executable code also to communicate a success message to a clinician application in response to receiving the acknowledgment message.

In one example embodiment, a medical device assembly is provided that includes a clinician programing device configured to communicate with an implanted medical device of a patient. The clinician programming device includes one or more processors configured to communicate program instructions related to a programming session of the implanted medical device, receive updated program instructions from a remote programming engine based on a simulation of operation of the implanted medical device based on the program instructions, and communicate updated program instructions to the implanted medical device based on the updated program instructions.

Optionally, the one or more processors are configured to receive communication related to initialization of the implantable medical device, related to whether the programming session is pending, and related to termination of the programming session. In one aspect, the one or more processors are additionally configured to determine whether the termination of the programming session is in response to completion of the programming session, or in response to a programming error. In another aspect the one or more processors are further configured to receive a message from a virtual device engine (VDE), the message including the updated program instructions for the programming session that is related to a treatment to be performed by the implanted medical device, receive an asynchronous remote programming profile from the VDE that includes the updated program instructions, and communicate the asynchronous remote programing profile to the implanted medical device. In one example, the one or more processors further configured to generate and display a pending message in response to communicating the asynchronous remote programing profile and present the pending message until an acknowledgment message is received from a patient application. In another example, the one or more processors further configured to display a success message in response to receiving the acknowledgment message. In yet another example, the one or more processors further configured to display a failure message in response to a timer reaching a determined period before receiving the acknowledgment message.

In one example embodiment, a medical device remote-control (MDRC) system is provided that includes a clinician electronic device having one or more processors configured to communicate a request to an engine over a network to enter a communication session with a remote electronic device and generate an authentication code. The one or more processors are also configured to provide a pathway for the communication session based on the authentication code. The remote electronic device can also have one or more processors configured to obtain the authentication code, verify the authentication code via the engine and provide the pathway for the communication session.

Optionally, the pathway includes the engine. In one aspect, the one or more processors of the clinician electronic device are further configured to obtain instructions from a clinician application of the clinician programming device and perform the communicate, generate, and provide steps based on the instructions. In another aspect, the one or more processors of the remote electronic device are further configured to obtain instructions from a remote-controlled (RC) application, and perform the obtain, verify, and provide steps based on the instructions. In one example, the one or more processors of the clinician electronic device are further configured to communicate the authentication code to the engine. In another example, the one or more processors of the remote electronic device are further configured to obtain the authentication code from an input of an RC user, receive the authentication code from the engine, and verify the authentication code from the input of the RC user with the authentication code received from the engine.

Optionally, the one or more processors of the clinician programming device are further configured to communicate with a medical device. In one example, the medical device is an implantable medical device. In one aspect, the one or more processors of the clinician electronic device are further configured to provide a home page at an interface of the clinician programming device in response to loss of connectivity. In another aspect, the one or more processors of the remote electronic device are further configured to provide a home page at an interface of the remote electronic device in response to a termination of the communication session. In another example, the engine logs information related to the communication session in response to termination of the communication session.

In one example embodiment a method for treatment of a patient utilizing a medical device remote-control (MDRC) system is provided that includes communicating from a clinician electronic device a request to an engine over a network to enter a communication session with a remote electronic device and generating, with one or more processors of the clinician electronic device, an authentication code. The method also includes providing, with the one or more processors of the clinician electronic device, a pathway for the communication session based on the authentication code, and obtaining, with one or more processors of the remote electronic device, the authentication code. The method also includes verifying, with the one or more processors of the remote electronic device, the authentication code, and providing, with the one or more processors of the remote electronic device, the pathway for the communication session based on the authentication code.

Optionally, the method also includes forming the pathway between the clinician electronic device and remote electronic device via the engine. In another aspect, the method also includes obtaining, with the one or more processors of the clinician electronic device, instructions from a clinician application of the clinician electronic device, and performing the communicating, generating, and providing steps of the clinician electronic device based on the instructions. In one example, the method also includes obtaining, with the one or more processors of the remote electronic device, instructions from a remote-controlled (RC) application of the remote electronic device, and performing the obtaining, verifying, and providing steps of the remote electronic device based on the instructions. In another example, the one or more processors of the remote electronic device obtains the authentication code from an input of an RC user. Alternatively, the one or more processors of the remote electronic device receive a communication from the engine that includes the authentication, and wherein verification of the authentication code obtained from the input of the RC user is based on the authentication code received from the engine.

Optionally, the method also includes communicating, with the one or more processors of the clinician electronic device, with a medical device. In another aspect the method also includes providing treatment instructions to the medical device based on the communication session and providing treatment with the medical device based on the treatment instructions. In one example, the method additionally includes providing, with the one or more processors of the clinician electronic device, a home page at an interface of the clinician electronic device in response to loss of connectivity at the clinician electronic device. In another example, the method further includes providing, with the one or more processors of the remote electronic device, a home page at an interface of the remote electronic device in response to termination of the communication session. In yet another example, the method also includes logging, with the engine, information related to the communication session in response to termination of the communication session.

DETAILED DESCRIPTION

Figure 1:
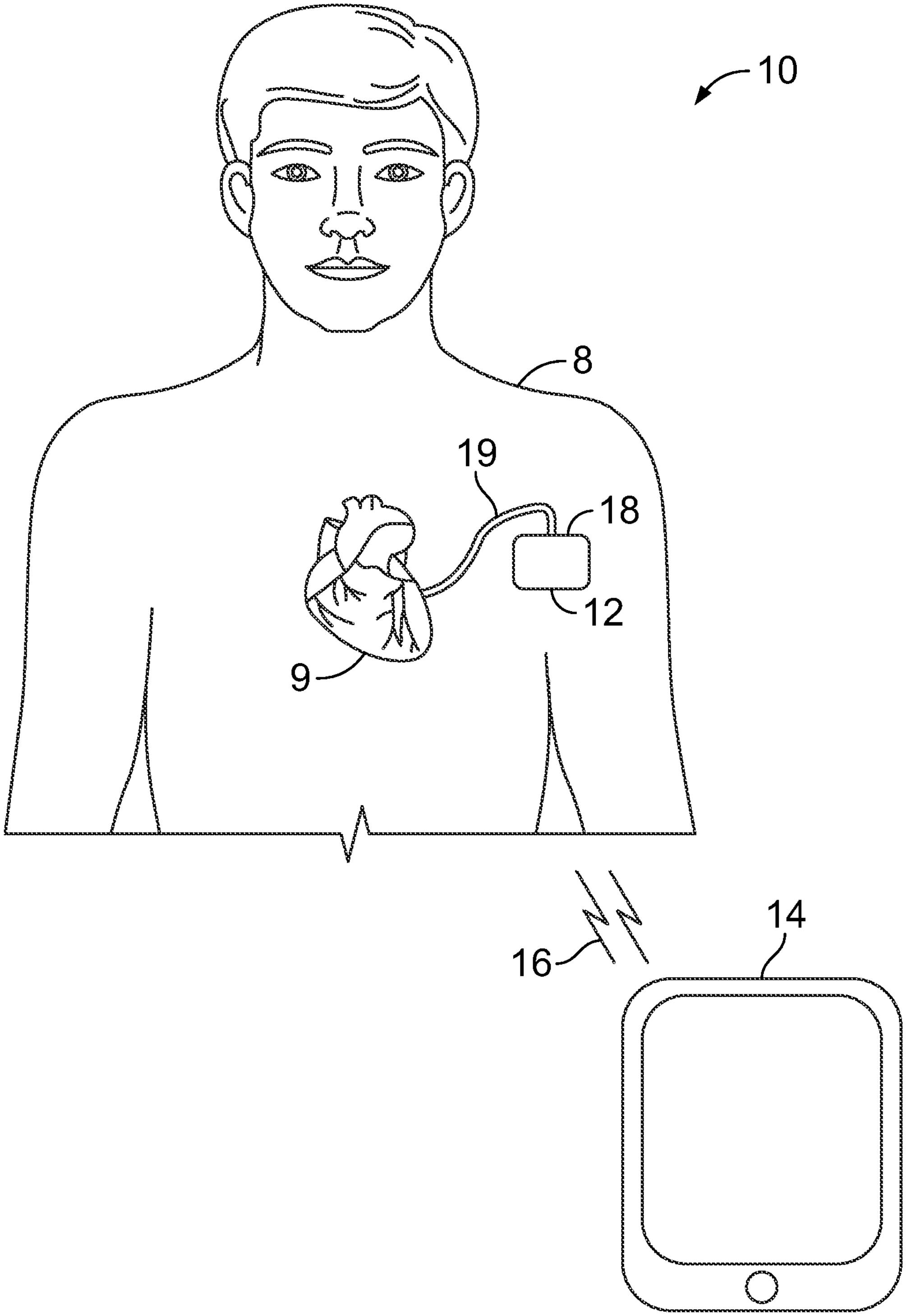
FIG. 1 illustrates a simplified block diagram of a system operated in accordance with embodiments herein.

Embodiments herein provide methods and systems that are designed to enhance integrity and authenticity of wireless programming communications between one or more external devices and an IMD.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

The term "clinician programming device", as used herein refers to any and all electronic devices utilized by a clinician, technician, physician, caregiver, nurse, doctor, or the like. The electronic device can be a central processing unit (CPU), desktop computer, laptop computer, tablet, smartphone, smart watch, monitor console, etc. The electronic device includes one or more processors configured to follow instructions, and a transceiver configured to communicate over a network, in a cloud, over Bluetooth (BLE), wirelessly, over the air, through a wire, or the like. In one example, the clinician programming device communicates with a patient programming device. In another example, the clinician programming device is local to the patient, and can communicate with an implanted medical device of a patient. In this manner, the clinician programming device can be located locally at the patient, or remotely and communicate with a patient programming device.

The term "patient programming device", as used herein refers to any and all electronic devices utilized by a patient to monitor or make determination related to the IMD of the patient. The electronic device can be a central processing unit (CPU), desktop computer, laptop computer, tablet, smartphone, smart watch, monitor console, etc. The electronic device includes one or more processors configured to follow instructions, and a transceiver configured to communicate over a network, in a cloud, over Bluetooth (BLE), wirelessly, over the air, through a wire, or the like. In one example, the patient programing device communicates with a clinician programming device.

The term "remote electronic device", as used herein refers to any and all electronic devices that are not located at a patient. The remote electronic device must communicate with an electronic device, programming device, or the like at the location of the patient over a network, mesh network, wirelessly, wired, or the like. In one example the remote electronic device is a remote-controlled (RC) electronic device. In another example, the clinician programming device can be considered a remote electronic device. Alternatively, the remote electronic device communicates with a clinician electronic device can be local to a patient, and in communication with the remote electronic device. A clinician electronic device is configured to be operated by a clinician, whereas the remote electronic device can be operated by a clinician, a clinician support representative, etc. In particular, the remote electronic device communicates with the local electronic device (e.g., clinician electronic device, patient programming device, or the like) via an engine, a remote programming engine (RPE), or the like.

The term "communication session" is any period of time dedicated to communication between electronic devices over a network, mesh network, wirelessly, wired, etc. to provide information and data between a patient and medical personnel (e.g., clinician) or between two or more medical personnel (e.g., clinician and clinician support representative). In one example the communication session is a programming session and can be related to the operation of an IMD based on a set of instructions to provide a treatment. The set of instructions can be stored in a storage device of the IMD or communicated to the IMD. The set of instructions can include a treatment, pacing pattern, etc. for the IMD, and the IMD operates during the programming session based on those instructions. The programming session begins with the program instructions that are provided, uploaded, communicated, etc. (e.g., updated program instructions) and the IMD begins operating based on the set of instructions. The programming session ends when the IMD stops using the set of instructions for operation. In example embodiments, the IMD can terminate a session as a result of receiving a new set of instructions, an updated set of instructions, a change to the set of instructions, varying the set of instructions, or the like. In an alternative embodiment, the communication session can occur between a local electronic device such as a local clinician electronic device, and a remote electronic device. In an example, the communication session between the clinician electronic device and remote electronic device is conducted via an engine. In another example, the local electronic device of the communication session can be a patient programming device while a clinician programming device is considered the remote electronic device.

The term "simulate operation" as used here in relation to an IMD refers to producing a computer model of the operation of the IMD based on the current set of instructions that the IMD has, combined with any changes, updates, etc.

of the instructions requested. By creating the computer model, a check can be provided before communicating the update, changes, etc. to ensure the update, changes, etc. are to the most recent set of instructions at and IMD and will not cause error.

The term "initialization" as used herein refers to the preparation of an electronic device for operation in which diagnostic test are run, and the operating system is loaded. The initialization of an electronic device must occur before any changes, updates, or the like can be installed, provided, communicated, etc. to the operating system of the electronic device.

The term "virtual device engine" (VDE) as used herein refers to a simulation, or computer model stored within a cloud, network, or the like that can be utilized to represent an IMD. The VDE can be utilized to replicate, or simulate the operation of the IMD, including how an update, change, etc. to a programming session, or set of instructions will occur at an IMD prior to the update, change, etc. being communicated to the IMD. In this manner the VDE can be utilized to adjust, change, update, etc. the update, change, etc. to be communicated based on the VDE.

The term "asynchronous remote programming profile" as used herein refers to unique, custom, or varied program instructions (e.g., updated program instructions) for an IMD of an individual patient formed at a location other than within the IMD. The asynchronous remote programming profile includes any changes, variations, updates, or the like to update program instructions that are made as a result of simulations made from the VDE.

The term "obtains" and "obtaining", as used herein in connection with data, signals, information, and the like, include at least one of i) accessing memory of an external device or remote server where the data, signals, information, etc. are stored, ii) receiving the data, signals, information, etc. over a wireless communications link between the IMD and a local external device, and/or iii) receiving the data, signals, information, etc. at a remote server over a network connection. The obtaining operation, when from the perspective of an IMD, may include sensing new signals in real time, and/or accessing memory to read stored data, signals, information, etc. from memory within the IMD. The obtaining operation, when from the perspective of a local external device, includes receiving the data, signals, information, etc. at a transceiver of the local external device where the data, signals, information, etc. are transmitted from an IMD and/or a remote server. The obtaining operation may be from the perspective of a remote server, such as when receiving the data, signals, information, etc. at a network interface from a local external device and/or directly from an IMD. The remote server may also obtain the data, signals, information, etc. from local memory and/or from other memory, such as within a cloud storage environment and/or from the memory of a workstation or clinician external programmer.

The term "engine" as used herein refers to a any processor, electronic device with a processor, server, or the like within a cloud, network, etc. configured to communicate with electronic devices via a network, mesh network, wirelessly, wired, or the like that can make determinations. In one example, the engine can be a remote programming engine (RPE) that communicates with a clinician programming device. In another example, the RPE communicates between a clinician programming device, and a remote electronic device.

Provided by FIGS. 1-10 is a system for communicating with, and programming a medical device, such as an implantable medical device (IMD), over a network. Within the network, and in one example, within a cloud, a virtual device engine (VDE) is provided that receives communications from the IMD related to the programming status of the IMD, including pending updates, updates previously provided, and the like. When a clinician provides a medical device assembly for remotely programming an IMD of a patient. The medical device assembly includes a clinician programming device with a clinician application that communicates with an IMD of a patient, and a patient application at a patient programming dated program instructions for the IMD through the clinician application, the VDE simulates the IMD programming to determine whether updated program instructions are compatible with the current programming of the IMD. Based on the simulation, an asynchronous remote programming profile is generated for updating the IMD. In this manner, the IMD cannot be incorrectly updated by a clinician that does not have knowledge of the current programming status of the IMD.

FIG. 1 illustrates a simplified block diagram of a system 10 operated in accordance with embodiments herein. The system 10 includes an IMD 12 and one or more external devices or instruments. A single external device 14 is illustrated in FIG. 1. The IMD 12 and the external device 14 are configured to communicate with one another wirelessly over a wireless communication link 16. In an embodiment, the external device 14 updates an operating configuration of the IMD 12 by transmitting a programming package to the IMD 12 along the communication link 16. The embodiments described herein provide an algorithm or workflow for verifying the validity, integrity, and authenticity of configuration change requests of the programming package, including a set of instructions of the programming package, prior to executing the configuration change requests to update the operating configuration (e.g., programming session) of the IMD. For example, a configuration change for an implantable pacemaker or cardioverter defibrillator may represent a change in sensitivity threshold, a change in heart rate thresholds for binning atrial fibrillation or tachycardia events, a change in the number of arrhythmia events that should occur before delivering a therapy, a change in communications gain, a change in a communications protocol, or the like. A configuration change of a programming session may include updates to executing operations of importance for diagnosis and/or clinical care, such as lead impedance testing, testing for level of sensing, or even disabling device operations as part of palliative care.

The IMD 12 is implanted within a patient 8 at a site near the heart 9. The IMD 12 may be a cardiac pacemaker, an implantable cardiac monitoring device (ICM), a defibrillator, an ICM coupled with a pacemaker, or the like. The IMD 12 is intended for implantation within a subcutaneous pocket of the patient. The IMD 12 may be configured to sense cardiac signals to monitor cardiac activity over time. Optionally, the IMD 12 may also be configured to deliver stimulation therapy to the heart 9. For example, the IMD 12 may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto.

The IMD 12 in the illustrated embodiment includes a body or housing 18 that is connected to at least one lead 19. A single lead 19 is shown in FIG. 1, but the IMD 12 may include multiple leads in another embodiment. The lead 19 extends from the housing 18 to the heart 9, such that the distal end is in contact with patient tissue surrounding the heart 9. The lead 19 includes one or more electrodes that may measure cardiac signals of the heart 9 and deliver stimulation therapy to the heart 9. In an embodiment, a single electrode may emit a stimulation pulse in a stimulation mode, and then may quickly switch to a monitoring mode to detect cardiac signals following the stimulation pulse.

Although the IMD 12 in the illustrated embodiment includes a lead 19, one or more of the embodiments described herein utilize a leadless IMD that does not include any lead. For example, the IMD 12 may be a leadless pacemaker, a leadless cardiac monitoring device (ICM), or the like. In general, the IMD 12 may represent a cardiac monitoring device, pacemaker, cardioverter, cardiac rhythm management device, defibrillator, neurostimulator, leadless monitoring device, leadless pacemaker, and the like. For example, the IMD may include one or more structural and/or functional aspects of the device(s) described in U.S. Pat. No. 9,333,351 "Neurostimulation Method And System To Treat Apnea"; U.S. Pat. No. 9,044,610 "System And Methods For Providing A Distributed Virtual Stimulation Cathode For Use With An Implantable Neurostimulation System"; U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; and U.S. application Ser. No. 15/973,249, titled "Single Site Implantation Methods For Medical Devices Having Multiple Leads", filed May 7, 2018, which are hereby incorporated by reference in their entireties. Additionally or alternatively, the IMD may be a leadless implantable medical device (LIMD) that include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference. Additionally or alternatively, embodiments may be implemented utilizing all or portions of the methods and systems described in U.S. application Ser. No. 16/930,791, filed Jul. 16, 2020 and titled "METHODS, DEVICES AND SYSTEMS FOR HOLISTIC INTEGRATED HEALTHCARE PATIENT MANAGEMENT".

In another example, the IMD 12 may be an ICM that includes one or more structural and/or functional aspects of the device(s) described in U.S. patent application Ser. No. 15/084,373, filed Mar. 29, 2016, entitled, "Method And System To Discriminate Rhythm Patterns In Cardiac Activity," which is expressly incorporated herein by reference. All references, including publications, patent applications and patents, cited herein are hereby incorporated by reference to the same extent as if each reference were individually and specifically indicated to be incorporated by reference and were set forth in its entirety herein.

The housing 18 may contain a battery, pulse generation circuitry, communication circuitry, a data storage device (e.g., memory), and/or control circuitry including one or more processors. The control circuitry is for receiving and analyzing electrocardiogram IEGM signals from the electrodes 13. The control circuitry may include at least one processor for processing the IEGM signals in accordance with algorithms to make determinations about the state of the heart 9. The memory provides storage for the cardiac signals and programmed instructions for the control circuitry that provide a communication session that is a programming session. The battery powers the circuitry with the housing 10. For example, the battery powers the pulse generation circuitry to generate stimulation pulses and powers the communication circuitry to communicate with an external device 16. The control circuitry may generate messages to be communicated via the communication circuitry to the external device 14. The messages may include the IEGM signals and/or data generated based on the IEGM signals. The control circuitry is also configured to analyze messages, received via the communication circuit from the external device 14, that include programming packages for updating the operating configuration, including settings, parameters, behavior, and the like, of the IMD 12. Exemplary structure for the IMD 12 is discussed and illustrated below in connection with FIG. 2.

The external device 14 may represent a computing device that is accessible or possessable by the patient or a clinician, such as a tablet computer, a smartphone, a wearable device, laptop computer, a desktop computer, a bedside monitor installed in a patient's home, or the like. The external device 14 alternatively may be a programmer device used in the clinic by a clinician. The external device may be one of the devices listed above that is communicatively connected to a second external device that represents the source of the programming package intended to update the operating configuration of the IMD 12. For example, the second external device may be a server or another computing device that is communicatively connected to the first external device 14 via a network connection (e.g., the Internet). In general, the external device 14 facilitates access by physicians to patient data as well as permits the physician to review real-time electrocardiogram (ECG) signals and, as specifically described herein, update the operating configuration of the IMD 12 without the clinician being near the patient.

Figure 2:
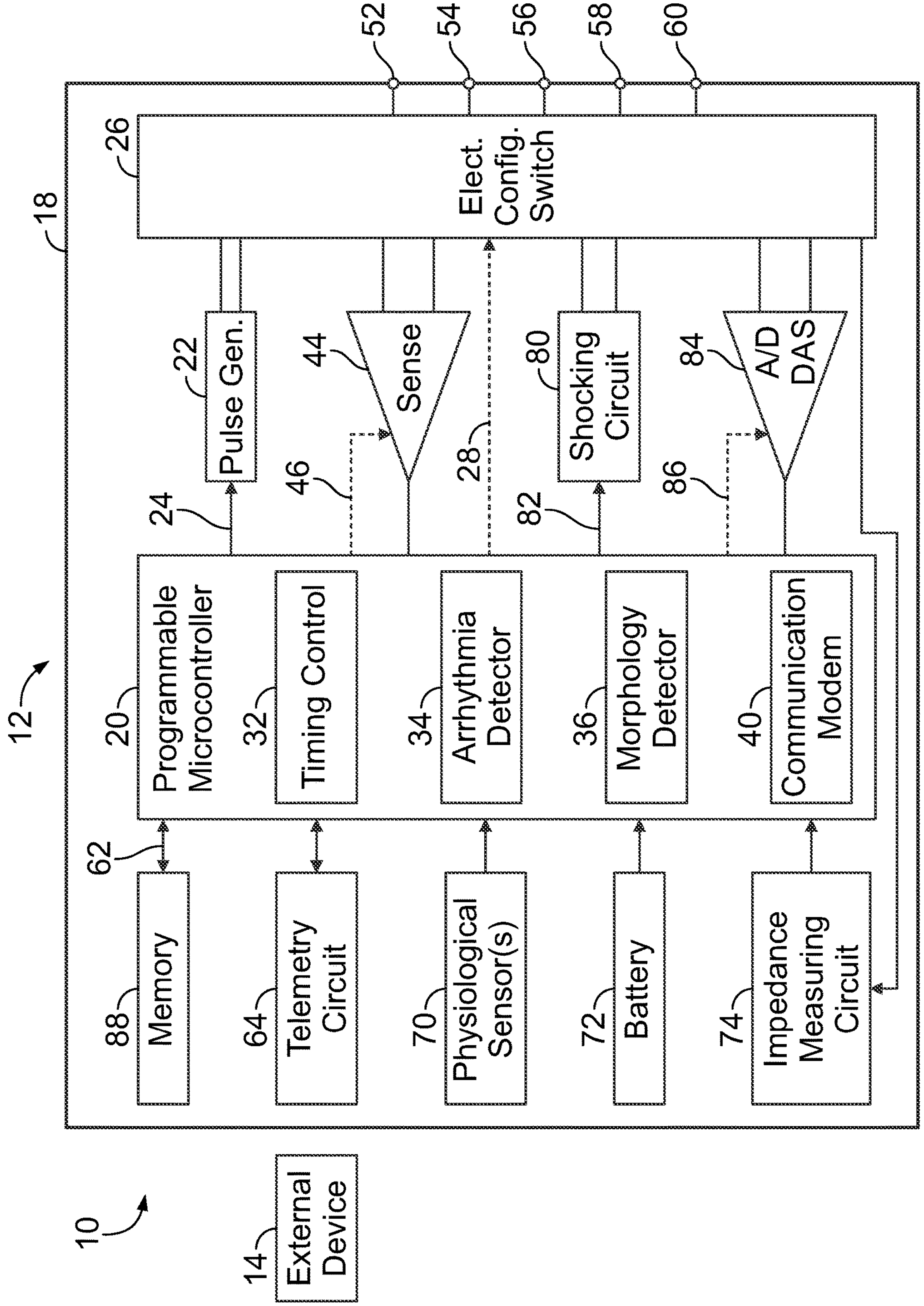
FIG. 2 shows a block diagram of the system of FIG. 1, according to an embodiment.

FIG. 2 shows a block diagram of the system 10 according to an embodiment. The housing 18 or case of the IMD 12 holds the electronic and/or computing components. The housing 18 further includes a connector (not shown) with at least one terminal 52 and optionally additional terminals 54, 56, 58, 60. The terminals may be connected to electrodes that are located in various locations within and about the heart, such as on the lead 19 (shown in FIG. 1). The electrodes may include various combinations of ring, tip, coil, shocking electrodes, and the like.

The IMD 12 includes a programmable microcontroller 20 that controls various operations of the IMD 12, including cardiac monitoring and stimulation therapy. Microcontroller 20 includes a one or more processors (e.g., a microprocessors or equivalent control circuitry), RAM and/or ROM memory, logic and timing circuitry, state machine circuitry, and I/O circuitry. Microcontroller 20 includes an arrhythmia detector 34 that is configured to detect cardiac activity data to identify potential atrial fibrillation (AF) episodes as well as other arrhythmias (e.g., Tachycardias, Bradycardias, Asystole, etc.).

An electrode configuration switch 26 is optionally provided to allow selection of different electrode configurations under the control of the microcontroller 20. The electrode configuration switch 26 may include multiple switches for connecting the desired electrodes to the appropriate I/O circuits, thereby facilitating electrode programmability. The switch 26 is controlled by a control signal 28 from the microcontroller 20. Optionally, the switch 26 may be omitted and the I/O circuits directly connected to a housing electrode.

The IMD 12 may include a chamber pulse generator 22 that generates stimulation pulses for connecting the desired electrodes to the appropriate I/O circuits, thereby facilitating electrode programmability. The pulse generator 22 is controlled by the microcontroller 20 via control signals 24. The IMD 12 includes a sensing circuit 44 selectively coupled to one or more electrodes that perform sensing operations through the switch 26 to detect cardiac activity. The sensing circuit 44 may include dedicated sense amplifiers, multiplexed amplifiers, or shared amplifiers. The sensing circuit 44 may operate in a unipolar sensing configuration or a bipolar sensing configuration. The output of the sensing circuit 44 is connected to the microcontroller 20 which, in turn, triggers, or inhibits the pulse generator 22 in response to the absence or presence of cardiac activity. The sensing circuit 44 receives a control signal 46 from the microcontroller 20 for purposes of controlling the gain, threshold, polarization, and timing of any blocking circuitry (not shown) coupled to the sensing circuit.

The IMD 12 further includes an analog-to-digital A/D data acquisition system (DAS) 84 coupled to one or more electrodes via the switch 26 to sample cardiac signals across any pair of desired electrodes. The A/D DAS 84 is controlled by a control signal 86 from the microcontroller 20.

The IMD 12 is further equipped with a communication modem (modulator/demodulator) or circuit 40 to enable wireless communication. The modem 240 enables timely and accurate data transfer directly from the patient to the external device 14, and vice-versa. For example, the communication modem 40 is configured to establish the communication link 16 with the external device 14. In an embodiment, the communication modem 40 receives a programming package from the external device 14 and conveys the programming package for updating, changing, varying, etc. the IMD during a programming session to the microcontroller 20 for verification prior to executing configuration change requests and/or command execution requests contained within the programming package. In addition to remote programming of the IMD 12, the wireless communication link 16 with the external device 14 facilitates access by physicians and/or patients to patient data generated by the IMD 12.

The communication modem 40 may utilize radio frequency (RF), Bluetooth, or Bluetooth Low Energy telemetry protocols. The signals are transmitted in a high frequency range and will travel through the body tissue in fluids without stimulating the heart or being felt by the patient. The communication modem 40 may be implemented in hardware as part of the microcontroller 20, or as software/firmware instructions programmed into and executed by the microcontroller 20. Alternatively, the modem 40 may reside separately from the microcontroller 20 as a standalone hardware component.

The microcontroller 20 is coupled to a non-transitory data storage device, referred to herein as memory device 88, by a suitable data/address bus 62. The memory device 88 stores programmable operating parameters used by the microcontroller 20 and/or data associated with the detection and determination of arrhythmias. In an embodiment, the memory device 88 also stores the current programming session, along with any and all changes, modifications, updates, or the like previously made to the programming session.

The IMD 12 optionally includes one or more physiologic sensors 70 that adjust pacing stimulation rates, detect changes in cardiac output, changes in the physiological condition of the heart, and/or diurnal changes in activity (e.g., detecting sleep and wake states). Examples of physiological sensors 70 might include sensors that, for example, sense respiration rate, pH of blood, ventricular gradient, activity, body movement, position/posture, minute ventilation (MV), and/or the like.

The battery 72 provides operating power to all of the components in the IMD 12. The battery 72 is capable of operating at low current drains for long periods of time, and is capable of providing a high-current pulses (for capacitor charging) when the patient requires a shock pulse (e.g., in excess of 2 A, at voltages above 2 V, for periods of 10 seconds or more).

The IMD 12 further includes an impedance measuring circuit 74, which can be used for many things, including sensing respiration phase. The IMD 12 may be further equipped with a telemetry circuit 64 that can selectively communicate with an external device, such as the device 14, when connected via a physical (e.g., wired) communication link. The IMD 12 includes a shocking circuit 80 controlled by control signals 86 generated by the microcontroller 20. The shocking circuit 80 generates shocking pulses of low (e.g., up to 0.5 joules), moderate (e.g., 0.5-10 joules), or high energy (e.g., 11 to 40 joules), as controlled by the microcontroller 20. In an alternative embodiment in which the IMD 12 senses and monitors cardiac activity without administering stimulation therapy, the IMD 12 may lack the pulse generator 22 and the shocking circuit 80.

The microcontroller 20 may include other dedicated circuitry and/or firmware/software components, such as a timing control (module) 32 and a morphology detector (module) 36. The timing control 32 is used to control various timing parameters, such as stimulation pulses (e.g., pacing rate, atria-ventricular (AV) delay, atrial interconduction (A-A) delay, ventricular interconduction (V-V) delay, etc.) as well as to keep track of the timing of RR-intervals, refractory periods, blanking intervals, noise detection windows, evoked response windows, alert intervals, marker channel timing, and the like. The morphology detector 36 is configured to review and analyze one or more features of the morphology of cardiac activity signals, such as the morphology of detected R waves to determine whether to include or exclude one or more beats from further analysis.

Figure 3:
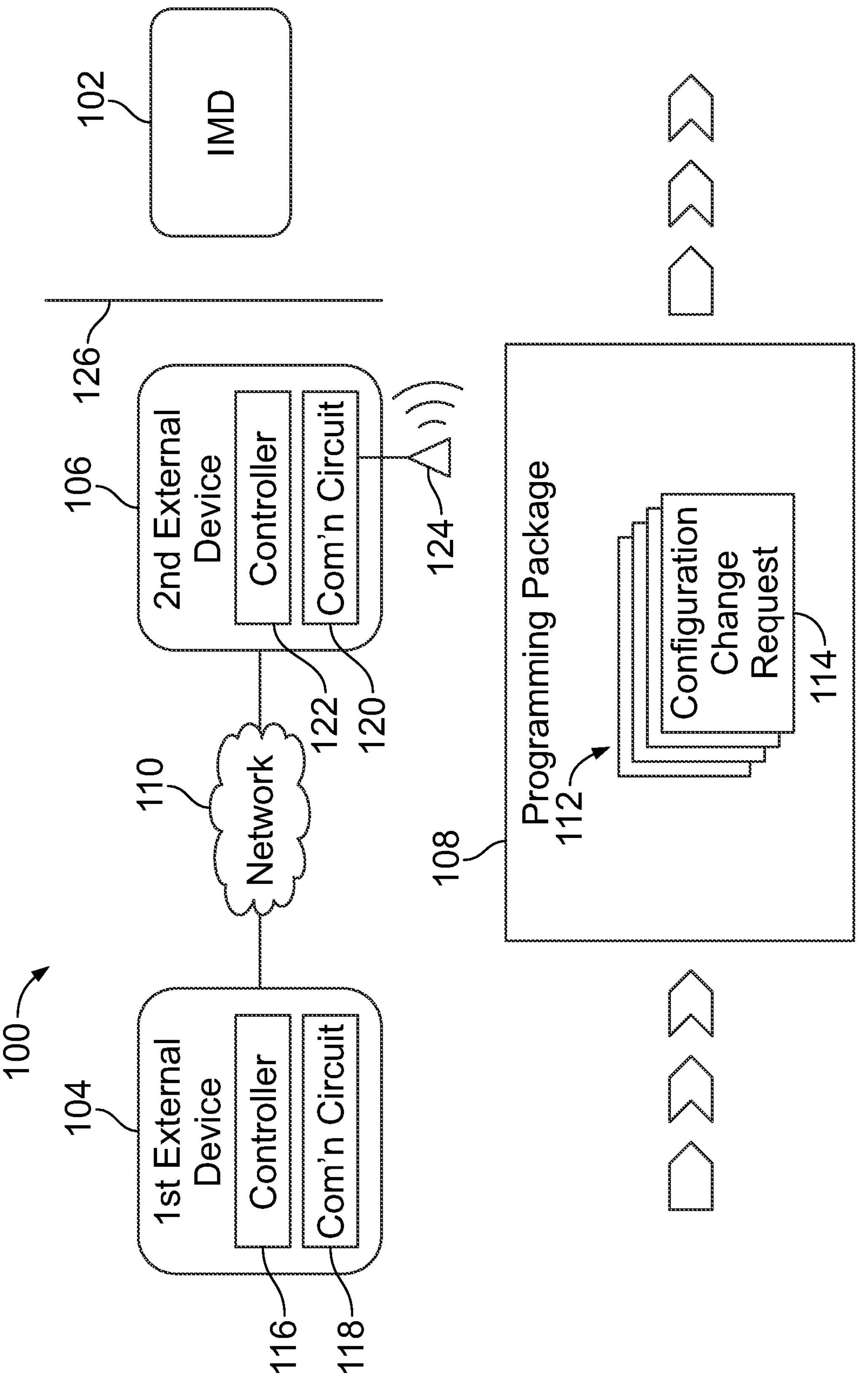
FIG. 3 is a schematic illustration of a system, according to an embodiment.

FIG. 3 is a schematic illustration of a system 100 according to an embodiment. The system 100 provides secure remote programming of an IMD 102 while the IMD 102 is implanted within a patient. In addition to the IMD 102, the system 100 includes one or more external devices. In the illustrated embodiment, the external devices include a first external device 104 and a second external device 106, but the system 100 may include only a single external device or more than two external devices in other embodiments. The system 100 may represent the system 10 shown in FIGS. 1 and 2. For example, the IMD 102 may represent the IMD 12 and the second external device 106 may represent the external device 14.

The one or more external devices build a programming package 108 that is designed to update an operating configuration of a programming session of the IMD 102. The operating configuration of the programming session of the IMD 102 generally refers to the specific settings, functions, parameters, and the like that dictate the device behavior. For example, the operating configuration affects how the IMD 102 collects data, such as cardiac signals, how the IMD 102 analyzes the data, and how the IMD 102 responds to the data. The response may include activating the pulse generator or shocking circuit to deliver stimulation therapy to the patient, saving data in the memory device, communicating data to the external device 106, or the like. Even if the IMD 102 has been previously programmed, the operating configuration of the programming session may be updated over time due to physiological changes in the patient, unplanned movement of the IMD 102 within the patient, or even to enhance functionality of the IMD 102 based on software developments.

In the illustrated embodiment, the first external device 104 builds the programming package 108 related to the programming session. In a non-limiting example, the first external device 104 is accessed and utilized by a clinician to select a collection 112 of multiple configuration change requests 114 for inclusion in the programming package 108. The first external device 104 may be a clinician programming device, a workstation, or a computing device (e.g., smartphone, tablet computer, laptop computer, etc.). The clinician may select the collection 112 by communicating via a network 110 with a server or other computing device in the cloud. For example, the clinician may be required log in to a secure portal prior to receiving access to select the configuration change requests 114 and command the generation of the programming package 108. The first external device 104 may be remote from the second external device 106 and the patient.

The first external device 104 conveys the programming package 108, as a message, to the second external device 106 via the network 110. In a non-limiting example, the second external device 106 is a device that is disposed proximate to the patient, at least at a time that the second external device 106 communicates the programming package 108 to the IMD 102. For example, the second external device 104 may be a bedside monitoring device or a computing device utilized or possessed by the patient, such as a smartphone, tablet computer, laptop computer, or the like.

When the second external device 106 receives the programming package 108, the programming package 108 may schedule a designated time in the future at which to transmit the programming package 108 to the IMD 102. The second external device 106 initially stores the programming package 108 in a memory device of the device 106 until the designated time. At the designated time, the second external device 106 wirelessly transmits the programming package 108 to the IMD 102 to update a programming session. This process of scheduling in advance the delivery of the programming package to the IMD via an intermediary device is referred to as asynchronous remote programming. The IMD 102 is implanted within the patient at the time that the IMD 102 receives the programming package 108. According to embodiments herein, the IMD 102 utilizes a virtual device engine (VDE) to simulate operation of the IMD based on the programming package. The VDE communicates with the IMD to ensure the most recent programming configuration is known. In this manner, the VDE can verify whether the programming package is configured and based on the most recent and most updated programming session at the IMD. If all of the elements of the programming package 108 are verified, then the IMD 102 executes all of the configuration change requests 114 to update the operating configuration of the IMD 102. On the other hand, if at least one of the elements are not verified, as described herein, then the IMD 102 does not execute any of the configuration change requests 114, such that the operating configuration of the IMD 102 is not updated based on the change request.

The first and second external devices 104, 106 include respective controller circuits (e.g., controllers) and communication circuits. Each of the controllers includes one or more processors. In the process described above, the controller 116 of the first external device 104 generates the programming package 108. The communication circuit 118 of the first external device 104 communicates the programming package 108 to the second external device 106 via the network 110. The communication circuit 120 of the second external device 106 receives the programming package 108 and conveys the package 108 to the controller 122 of the second external device 106 for analysis. The controller 122 determines the scheduled delivery time and transmission characteristics, such as frequency channel and protocol, for communicating the programming package 108 to the IMD 102. At the scheduled delivery time, the controller 122 utilizes the communication circuit 120 to transmit the programming package 108 to the IMD 102. The communication circuit 120 may include an antenna 124 that wirelessly transmits the programming package 108 via RF signals, such as Bluetooth. The signals that represent the programming package 108 penetrate the body 126 of the patient and reach a receiver of the IMD 102. The receiver may be the communication modem 40 shown in FIG. 2, which conveys the received data packets to the one or more processors of the microcontroller 20 for analysis. In this way, the IMD 102 is beneficially able to receive the programming package 108 without requiring a network connection or a proximity sensor.

In instances as described above in which the communication of the programming package 108 from the source to the IMD 102 is delayed and/or indirect, there is a risk that the contents of the programming package 108 may be tampered with or corrupted after generation and before receipt by the IMD 102. The system 100 and method described herein perform cryptographic operations to ensure that the configuration change requests 114 are immutable and that the source of the package 108 is authenticated prior to execution by the IMD 102.

Figure 4:
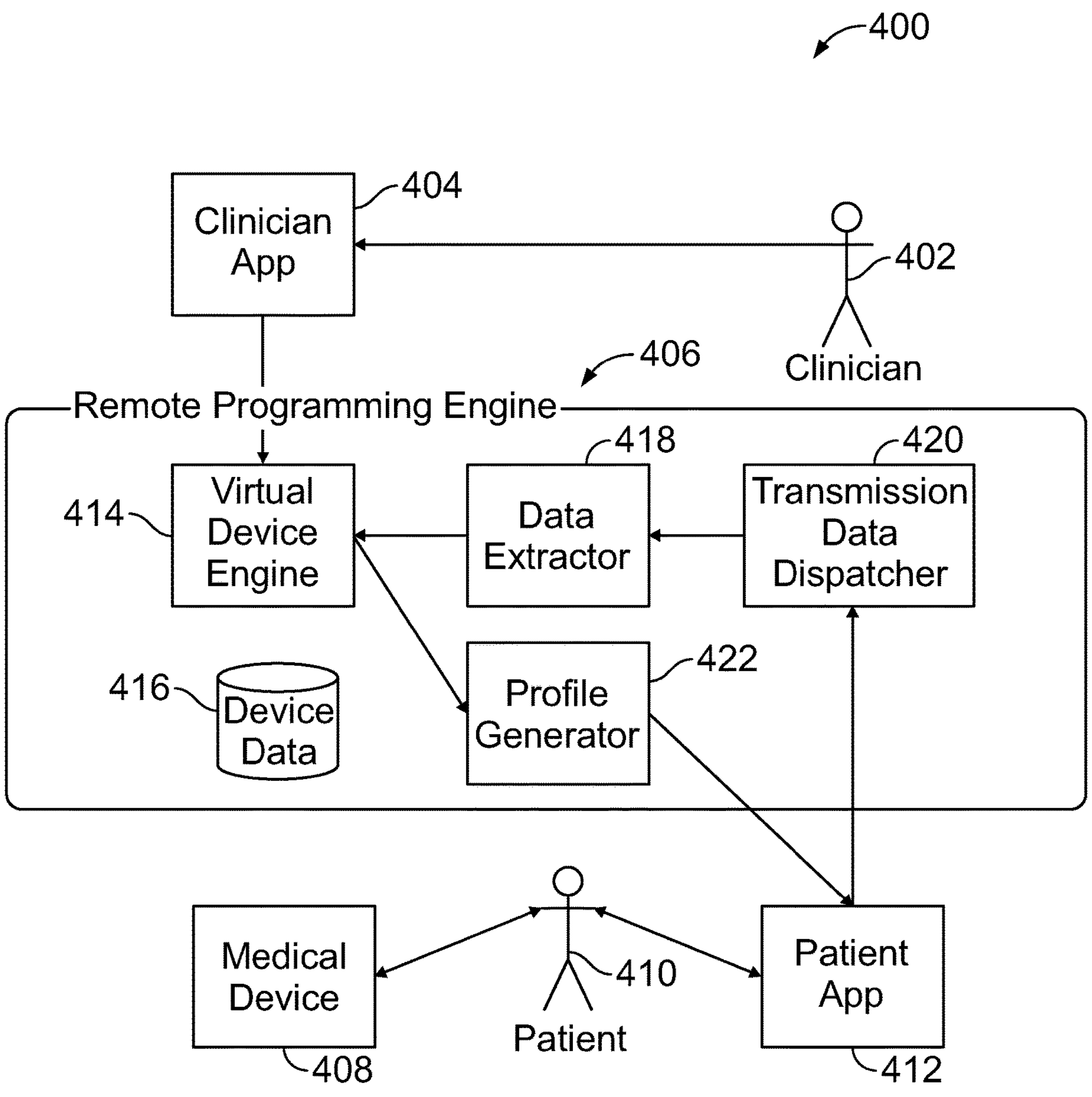
FIG. 4 is a schematic block diagram of a system for verifying an update sent by a clinician, according to an embodiment.

FIG. 4 illustrates a system 400 for verifying an update sent by a clinician 402 from a clinician application 404 through an RPE 406 to an IMD 408 of a patient 410 that utilizes a patient application 412. The patient application 412 in one example can be accessed and programmed at a patient programming device. The update may be an update of a treatment, software, firmware, application, program, etc. The clinician application 404 may be stored in a storage device of a clinician programming device, including a clinician laptop computer, desktop computer, CPU, smartphone, smartwatch, tablet, or the like. The clinician application 404 may also be stored within a network, such as in the cloud, at a server, at a network resource, or the like. In each instance, the clinician application includes instructions that may be executed by one or more processors. The one or more processors can be of the clinician laptop computer, desktop computer, CPU, smartphone, smartwatch, tablet, etc., of a server, of a network device, or the like. Based on the instructions, the steps of a method or process for updating the IMD are provided.

The RPE 406 may be in the cloud, in a network, at a server, over Bluetooth (BLE), or the like. The RPE 406 includes a VDE 414 that can simulate the operation of the IMD 408. By simulating the operation of the IMD 408, the VDE 414 obtains information related to the IMD 408, including all updates, changes, modifications, etc. that occur at the IMD 408 over time. The VDE 414 can then store this IMD 408 operational information at a device data store 416. In particular, the RPE 406 includes a data extractor 418 that extracts such information from a transmission data dispatcher 420 that continuously receives transmission data from the IMD 408 via the patient application 412.

By continuously obtaining the IMD data, the VDE 414 can continuously simulate the operation and device activities of the IMD 408, and store data at the device data store 416. The VDE can thus manage a communication session, including a programming session, implemented by the clinician 402 from initialization, to pending, to completed (whether successfully, or failure—see FIG. 5). In this manner, when the clinician app communicates the desired modifications, changes, updates, etc. to the RPE 406, the RPE can synchronize the current state of the IMD 408 with the modification, change, update, etc. desired to be implemented. The VDE 414 can then provide the synchronized data and information to an asynchronous profile generator 422 to generate an asynchronous remote programming profile that includes updated program instructions for updating the IMD 408. In this manner, if the IMD 408 has been modified previously without the knowledge of the clinician 402, the VDE 414 ensures the desired update occurs on the most recent version of a program, software, firmware, application, or the like.

Figure 5:
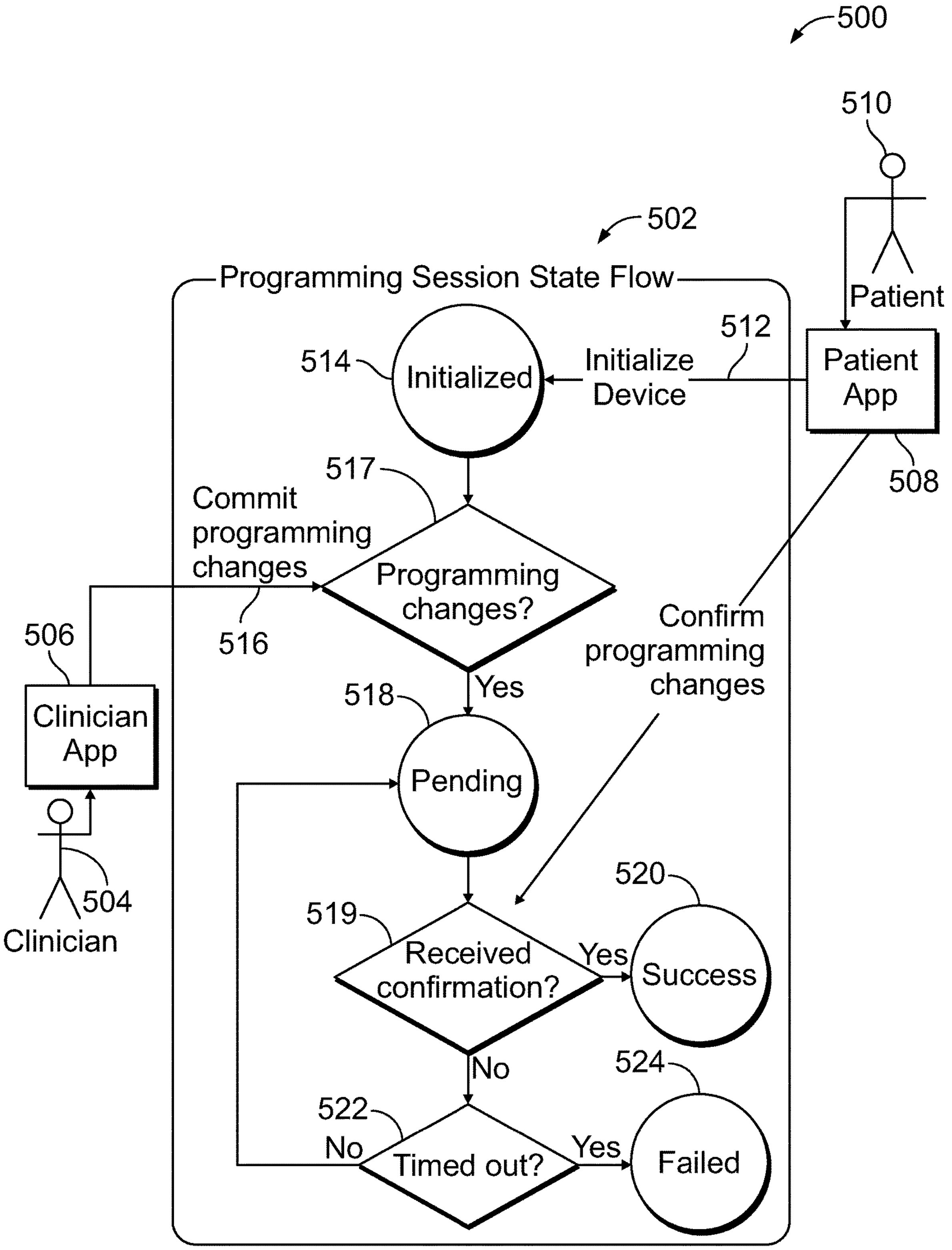
FIG. 5 is a schematic block flow diagram of a process for managing a programming session, according to an embodiment.

FIG. 5 illustrates a block flow diagram 500 of a VDE managing a programming session 502 as implemented by a clinician 504 via a clinician application 506, that in one example is at a clinician programming device. Similar to the embodiment of FIG. 4, the clinician programming device may be at a laptop computer, desktop computer, CPU, smart device, tablet, or the like. The clinician application may include instructions executed by one or more processors of the laptop computer, desktop computer, CPU, smart device, Tablet, or the like. Based on the programming session, a patient application 508 of a patient 510 receives updated program instructions for modifying, changing, updating, etc. a treatment, software, firmware, application, program, or the like. The patient application 508 can be at a patient programming device.

During the programming session 502, at 512, the VDE receives and input from a patient application initializing the IMD device. Thus, at 514 the VDE is initialized and ready for program changes. (See FIG. 6). At 516 the VDE receives the requested programming change from the clinician application 506. Then, at 517 a determination is made whether other programming changes have previously been made to the IMD, and whether initialization has occurred. If the patient has not initialized the IMD, the programming changes are not made. In this manner, the VDE prevents the updating of any and all operations, treatments, software, firmware, etc. until initialization has occurred. The initialization ensures the VDE has the most up to date data and information related to the IMD to prevent errors during the update.

If at 517, a determination is made that the IMD is initialized and the changes are appropriate, then the programming changes are implemented to the IMD, and a request for confirmation is provided. At this time, the VDE indicates the changes are pending, and at 518 a pending message may be displayed by the VDE on an electronic device of the patient via the patient application, or on an electronic device of the clinician via the clinician application. In this manner, the clinician and/or patient knows that changes to the IMD are underway.

At 519, while the VDE is still pending, a determination is made regarding whether the confirmation has been received. Once the confirmation of the update, or change is confirmed, then at 520, a success message can be communicated. Again, the success message can be communicated on an electronic device of either the clinician or patient.

If at 519, the VDE is not confirmed, then at 522 a determination is made whether a determined amount of time has lapsed. In particular, an amount of time may be calculated for an update to download, upload, result in a change, or the like. In one example this time may be fifteen minutes. As a result, the determined time may be one hour, such that if confirmation has not occurred in an hour, the update can be considered failed. While in one example one hour can be the determined period, in other examples two hours, a day, a week, etc. can be the determined period. Still, once the determined period is reached without confirmation, at 524 a failure message is provided. The failure message can be displayed at either or both of the clinician electronic device and/or the patient electronic device.

Figure 6:
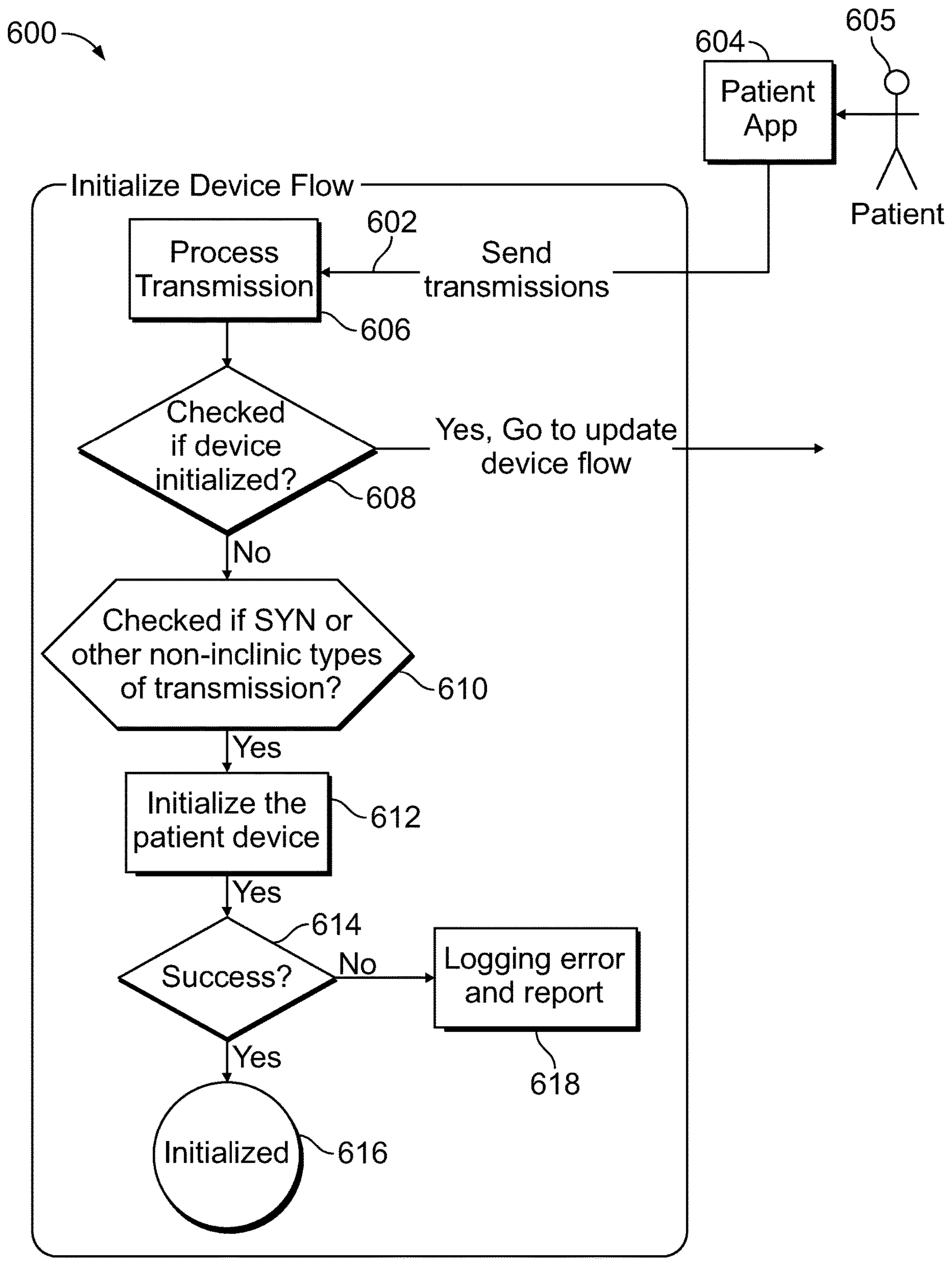
FIG. 6 is a schematic block flow diagram of process for initializing an IMD, according to an embodiment.

FIG. 6 illustrates an example of a process 600 for initializing an IMD in the VDE, and consequently the data store when a patient is not within a clinically setting. Clinical settings can include hospitals, clinics, doctor's offices, treatment centers, or the like. Consequently, the initialization can include a sync-up message, or non-clinic message that is communicated to the RPE, including from a patient application. The message is considered a sync-up message because the message ensures the VDE includes the most recent version of software, firmware, treatment, etc. at the IMD, including any provided in a clinic setting not using the clinician application.

At 602, a communication from a patient application 604 is transmitted to the VDE. In one example, the patient 605 may log into their patient application 604 and actuate an initialization button or key. At 606, the transmission is then processed and at 608, and a determination is made whether the IMD has already been initialized. If the IMD had previously been initialized, such as during an in-clinic visit, then no additional steps to be taken for initialization of the IMD.

If at 608, initialization has not previously occurred, then at 610, the VDE checks for sync messages, or other transmissions to the IMD. In particular, the VDE determines if any updates to treatments, software, firmware, or the like has occurred at the IMD without use of the VDE. In this manner, if any such updates have occurred, the VDE can find such transmissions and modify the currently requested update accordingly.

If at 610 a determination is made that no additional transmissions exist, then at 612 initialization of the IMD moves forward with no additional modifications or changes. However, if at 610 additional transmissions do exist, then at 612, the initialization of the IMD is based on the requested updates and the additional transmissions. In this manner, the requested updates are made based on the most recent data and information of the IMD.

Once initialization begins at 614, a determination is made whether such initialization was successful. If the initialization is not successful, then at 616 an error is logged by the VDE and an error message is communicated to the clinician application and the patient application. In this manner the patient and clinician understand an initialization failure has occurred and a log is provided for facilitating diagnosis of what caused the error.

If at 614, the initialization is determined to be successful, then at 616 the IMD is initialized. As a result of being initialized, the IMD can now be updated by the clinician application. If at 614 the initialization is determined to not be successful, then at 618 an error is logged and can be communicated to the patient application 604.

Figure 7:
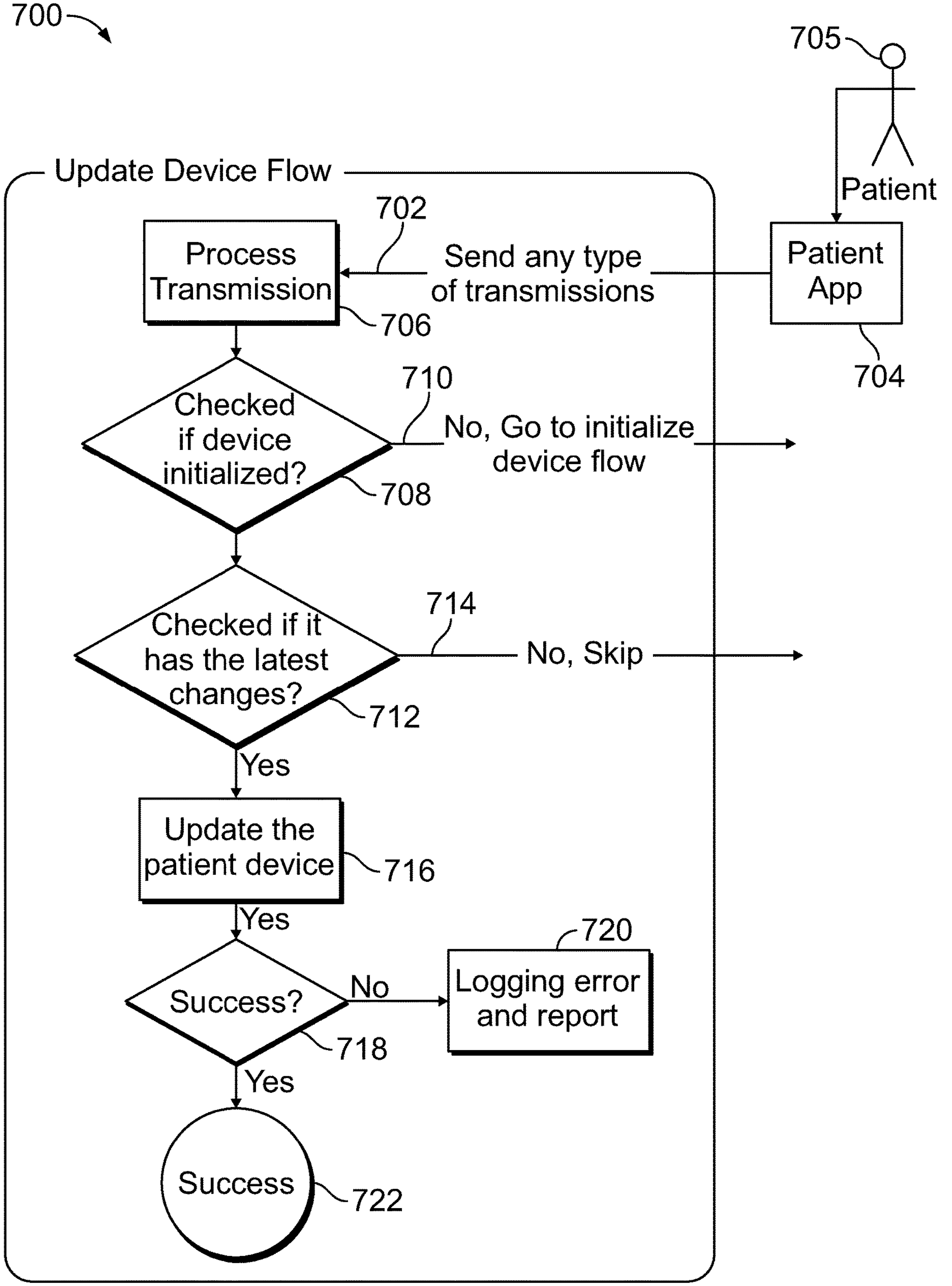
FIG. 7 is a schematic block flow diagram for updating and IMD, according to an embodiment.

FIG. 7 illustrates a block flow diagram of a process 700 of updating an IMD in a clinician setting. Again, the clinician setting may include a hospital, clinic, treatment center, doctor's office, or the like. When the IMD is updated in the clinical setting, such updates need to be communicated to the clinician application such that when an update is desired to be made using the clinician application, the most up to date data and information is available to the clinician application. In addition, any update provided utilizing the clinician application need to be known to the patient application, and IMD, so that changes in the clinic can be made with knowledge of all previous updates.

At 702, the patient application 704 communicates all communication transmissions received at the patient application 704 from a patient 705 to the VDE. At 706, each of the transmissions is processed. During processing, at 708, a determination is made whether the IMD has been initialized. If the device has not yet been initialized, then at 710 steps are taken to initialize the IMD consistent with the steps provided in FIG. 5. If at 708 the IMD is initialized, then at 712 a determination is whether the VDE includes the most recent updates, modifications, or changes to the IMD. If the VDE does not have the most recent updates, modification, or changes, then at 714, the IMD is not updated, and instead procedure is provided for receiving the most recent data and information.

If at 714 the most recent updates, modification, or changes are present, then at 716 the VDE updates the IMD. Once the IMD is set to be updated, at 718 a determination is made whether the update is successful. If at 718 the updating is not successful, then at 720 the error is logged, and an error message is communicated. If at 718 the updating is successful, then at 722 a success message is communicated.

Figure 8:
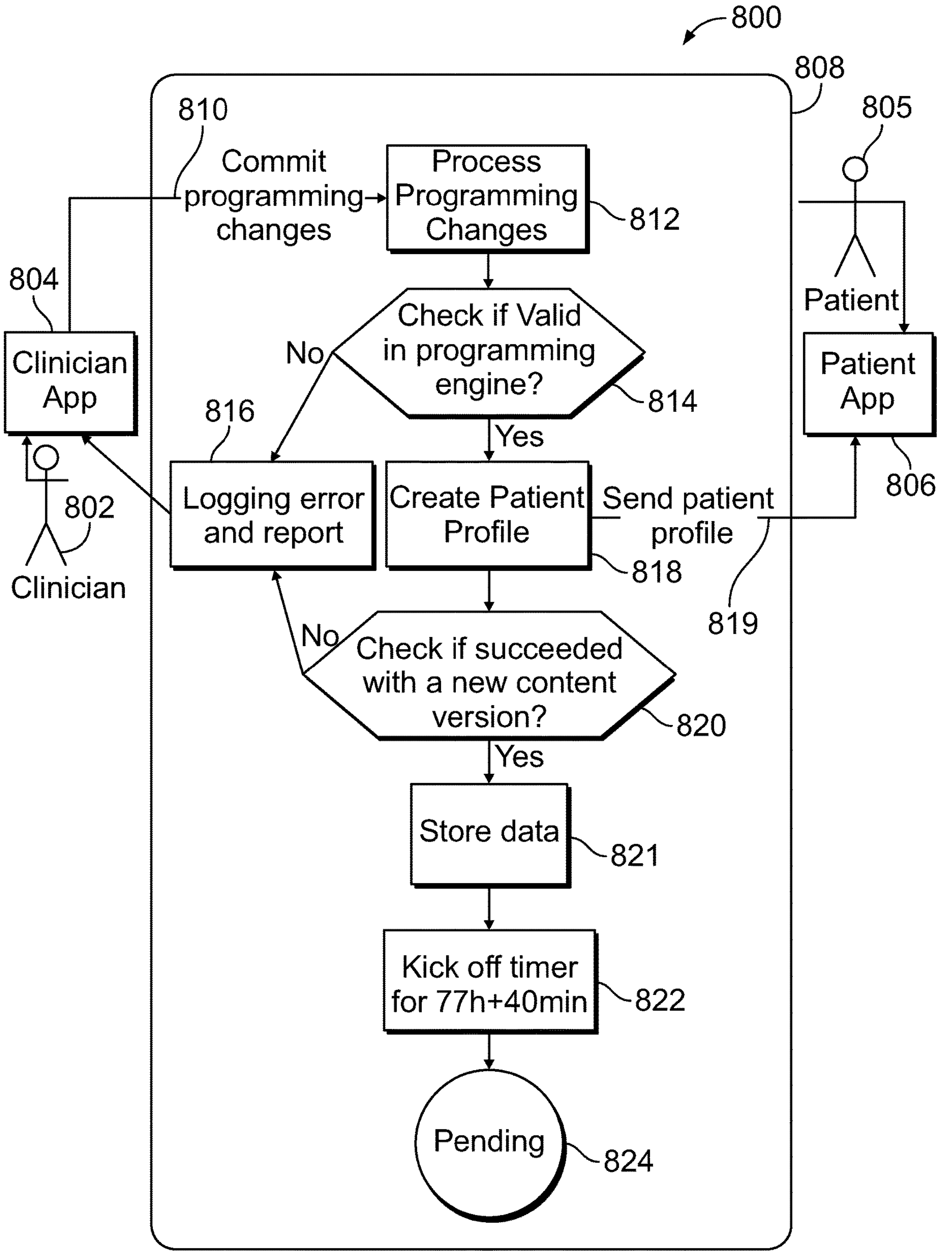
FIG. 8 is a schematic block flow diagram for a process for providing programming updates for an IMD, according to an embodiment.

FIG. 8 illustrates a block flow diagram for a process 800 where a clinician 802 provides programming updates for an IMD of a patient by providing a communication from a clinician application 804 that is received from a patient 805 via a patient application 806 through a VDE 808.

At the VDE 808, the VDE receives the programming changes 810, and at 812 processes the programing changes virtually. Because the VDE 808 communicates continuously with the patient application 806, when a change, update, etc. occurs at the patient application 806, such a change is communicated to the VDE 808 so that the VDE updates a virtual IMD that is representative of the patient IMD. As a result, the VDE can provide verification regarding whether the instructed programming change is allowable or will accomplish the desired outcome as desired by the clinician 802. In this manner, the VDE provides a check in case the IMD has been updated previously, and/or does not include the same configuration as the clinician application 804 indicates.

Therefore, at 814 a determination is made whether a prospective programing change is valid in the programming engine. If the programming change is not valid, then at 816 an error is generated, logged, and communicated to the clinician application 804. By logging the error and communicating the error to the clinician, the clinician can be made aware a change has previous occurred at the IMD that the clinician was not aware of at the time of the updated program instructions. This allows the clinician to determine the present condition of the IMD, and redetermine whether a change is desired. In one example, after determining the correct status of the IMD, a clinician may decide not to make the update or change previously desire. Alternatively, the clinician can update their programming records, and resubmit the request, only based on the correct version of the software, firmware, treatment schedule, or the like.

If at 814 a determination is made the prospective programming change is valid, then at 818 a patient profile is updated and communicated to the patient application as an asynchronous remote programming profile. If the updated program instructions are the first instructions provided for the IMD, the patient profile can be created. Alternatively, the patient profile is updated with the most recent update to form the asynchronous remote programming profile and communicated to the patient application at 819 so that the IMD can be updated.

After the patient profile is updated or created at 820 a determination is made whether the new content version was successful. If not, an error is logged and communicated. If at 820 the new content version is successful, the data is stored of the update at 821. In addition, at 822, when the updated program instructions are sent, the VDE automatically begins a timer and at 824 changes status to pending, and a pending message can be provided. In this manner, the VDE continuously checks to verify that the update has occurred. Thus, if another update is sent, and no verification that the update has occurred exists, the VDE can provide such information. Similarly, once the update is completed the message may be communicated to update the status of the VDE to provide a similar updated status. Alternatively, if the timer expires without receiving an acknowledgement message, a failure message can be displayed at a clinician programming device or patient programming device to alert the clinician, and/or patient that the update has not occurred.

Figure 9:
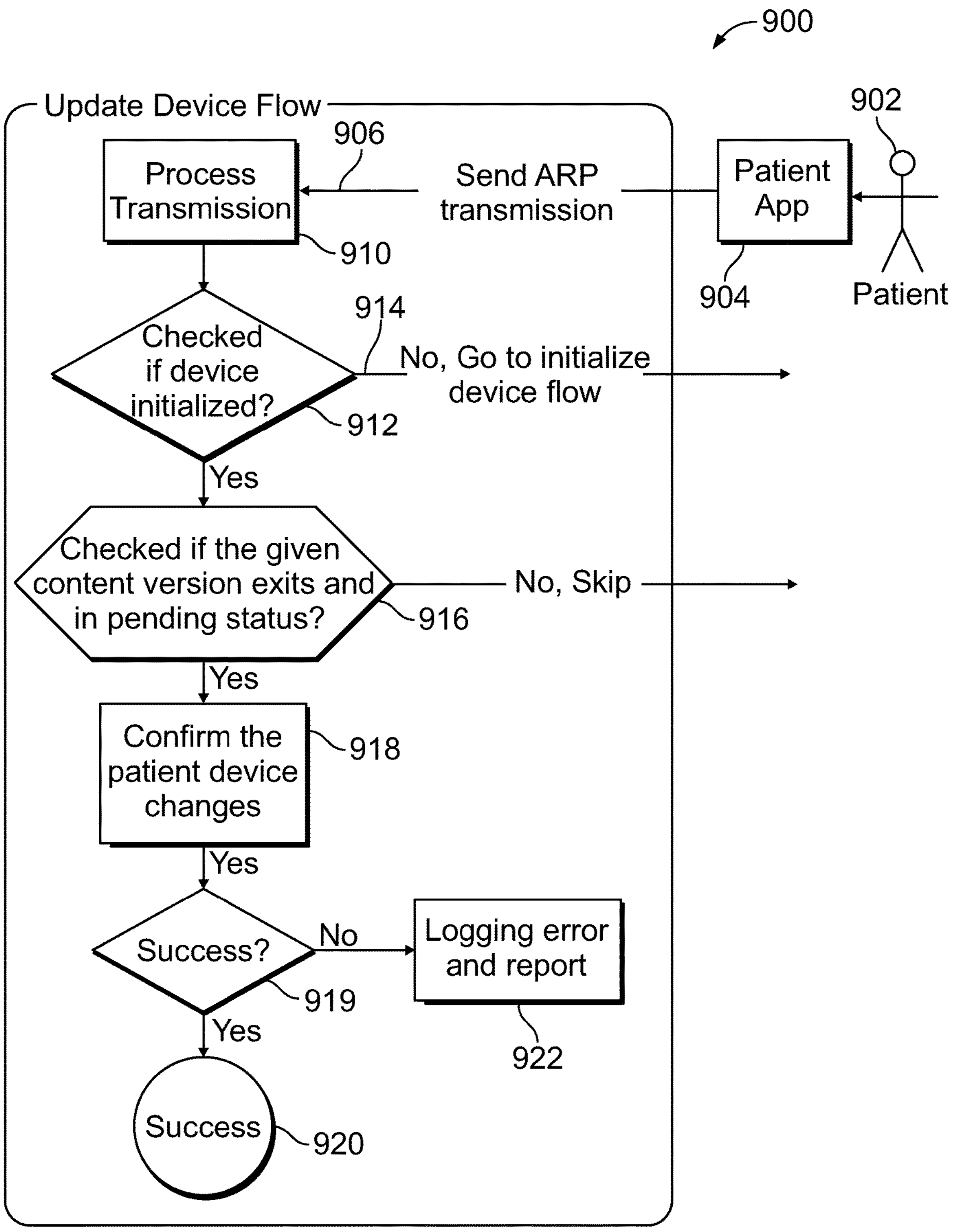
FIG. 9 is a schematic block flow diagram for a process updating an IMD, according to an embodiment.

FIG. 9 illustrates a process 900 for updating an IMD of a patient 902 using a patient application 904. In example embodiments, any of the previous systems, devices, methods, processes, etc. may be utilized to provide the update.

At 906 the patient application 904 transmits a message that includes an update to the IMD. At 910, the message is processed the VDE. After the message is process and a determination is made that the patient desires to make changes, update, etc. the IMD, at 912 a determination is made whether the IMD has be initialized for updating the IMD. Again, similar to other processes, the VDE also insures the IMD is initialized before any additional changes, updates, etc. can occur. If at 912 initialization has not previous occurred, then a message 914 is communicated to start the initialization process. If initialization has occurred, then at 916 a determination is made to see if an update is currently pending or if the content of the update already exists. If the content does not exist, or is not pending, then the rest of the process 900 can be skipped.

If at 916 the content exists, or is pending, then at 918 confirmation is requested by the VDE. In particular, the VDE verifies that the desired update, change, etc. has occurred. Therefore, at 919, a determination is made whether the update was successful. When successful, an acknowledgement message is communicated to the VDE at 920. In another example, a success message is displayed in response to receiving the acknowledgment message. If at 919 the update is not successful, then at 922 an error or failure message is communicated, and the error is logged.

Figure 10:
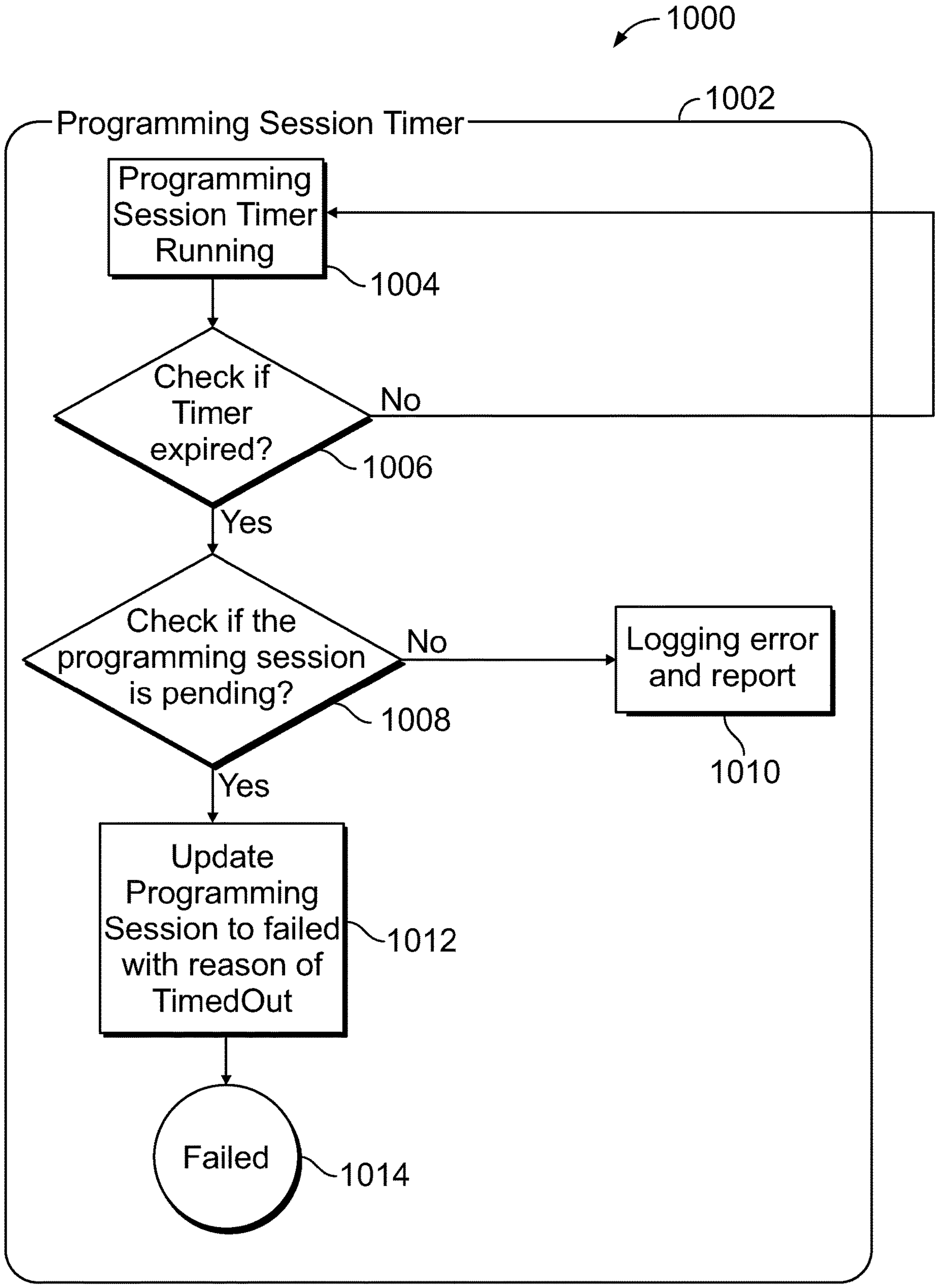
FIG. 10 is a schematic block flow diagram for using a timer for updating an IMD, according to an embodiment.

FIG. 10 illustrates a flow block diagram of a process 1000 that utilizes a program timer 1002 of a VDE to determine if an update, change, or the like has been implemented at an IMD. At 1004 the program timer begins running during a session. In one example, a clinician application is utilized to request a software update for the IMD. Upon verifying initialization of the IMD, the session timer begins to run for a determined period. The determined period can be determined based on the amount expected time for a change, update, etc. to occur. So, in an instance where software is being updated and is expected to take approximately one hour, the determined period can be two hours. In this manner, the determined period can be based on the expected time to complete a task, change, update, or the like. Alternatively, the determined period can be a static period of time, such as one day. Thus, regardless of the size of the update, whether expected to take five minutes, or five hours, the determined period can be a day. In other examples, the determined period can be two days, twelve hours, two hours, one week, etc. Still, the determined period begins when the change, update, etc. begins.

At 1006, a determination is made whether the timer has expired. The program session timer in one example is configured to check to see if the determined period has expired based on pre-set intervals. In one example, the pre-set interval can be one hour. Alternatively, the pre-set interval can be five minutes, two hours, etc. If the timer has expired, an error message may automatically be transmitted to notify a clinician, patient, etc. that the update was unsuccessful.

If the timer has expired, then at 1008 a determination is made whether a program session is still pending (e.g., whether an acknowledgement message has been received). So, if no acknowledgement message of completion of an update has been received by the VDE, the program session remains pending, the VDE continues to wait to receive the verification. Once the determined period has lapsed, if no acknowledgement message has been received, and the program session is no longer pending, at 1010 an error or failure message is logged into the data store and communicated to the clinician and/or patient. Without a confirmation, an error has occurred, and the failure message is communicated to provide notice to the clinician or patient. Alternatively, if the VDE is still pending at 1008, then at 1012 an updating failed message 1014 is communicated to either the patient and/or the clinician. Basically, after the determined period has lapsed with the status still pending, an assessment can be made that the update has failed.

FIGS. 11-16 illustrate an alternative embodiment of a system that utilizes an engine to provide medical care. In this embodiment, a medical device remote-control system (MDRC system) provides a secure, safe, end-to-end process for conducting remote device operations with a remote-control (RC) gateway (e.g., electronic device) connected to a medical device. During a communication session, a clinical support representative (remote user) can be authenticated and approved by the clinician (local user) before being granted the communication session. All communications and operations between the remote user and the local user through the supported connectivity protocols (including Cloud network and Bluetooth) are securely signed and encrypted. To this end, all such communication sessions can be recorded, and all operations can be logged.

The MDRC system consists of a cloud-based medical device remote-control (RC) application for remote users (i.e., clinical support representatives), a clinician application for local users (i.e., clinicians). The RC application manages data for users (clinicians and clinical support representatives), medical devices, and RC gateways (e.g., at electronic devices), and tracks communication sessions for operations. When a local user turns on a clinician electronic device, it will detect network connectivity and provide heartbeat information related to the clinician and clinician electronic device to a MDRC engine automatically. The clinician application on clinician electronic device displays system status and allows a local user to request a communication session in the MDRC system. The local user can start new a communication session on the clinician electronic device and can use an auxiliary electronic device such as a phone to communicate to the remote user an authentication code. After the remote user starts a remote session with the authentication code received via phone, the MDRC system authenticates the session request, and displays the Terms & Conditions (T&C) on an RC application for remote user. After the remote user opens the communication session the local user can confirm the request by accepting T&C and start to establish a new communication session with screen sharing. Eventually, the remote user will need to accept the T&C and start to view and control local user's screen for operating a medical device that is connected to a remote electronic device of the remote user.

Either the local user or the remote user can close a communication session. When a communication session is closed, session data can be saved in the MDRC engine, and both the local user and the remote user are notified. If an electronic device loses network connectivity, again, the communication session is closed automatically. Similarly, if there is no activity for a while, the MDRC system can also close the communication system automatically.

Figure 11:
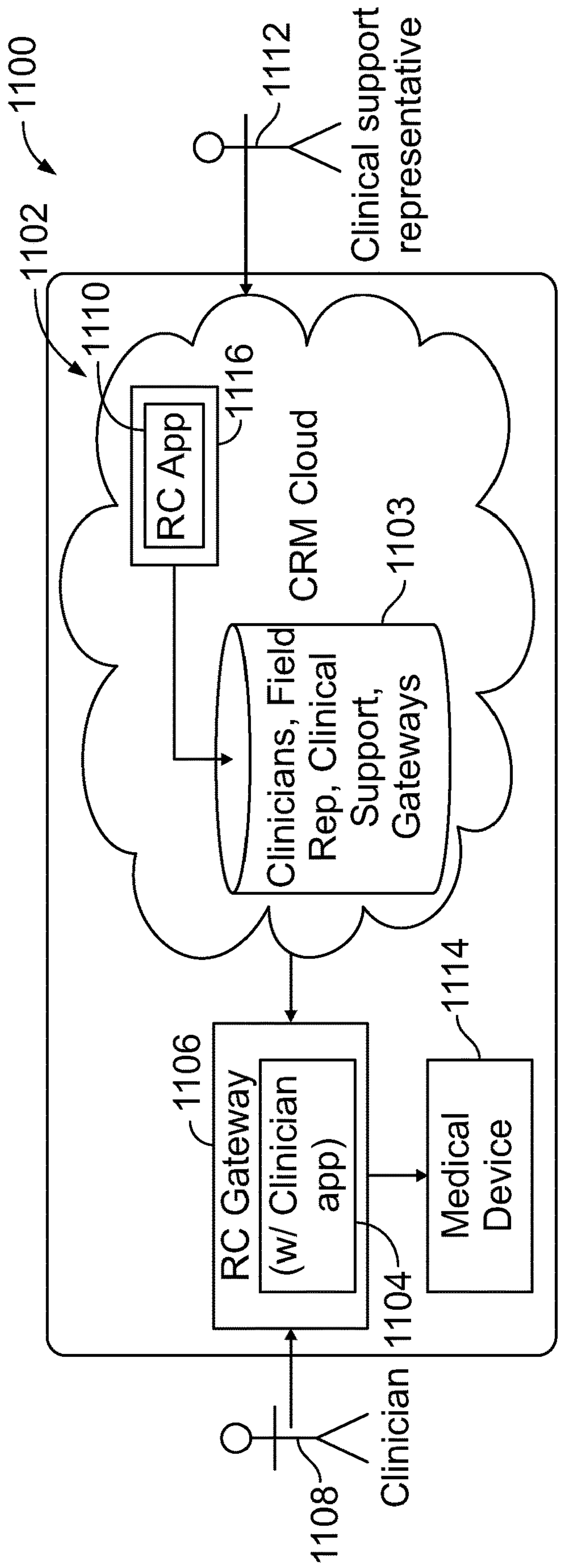
FIG. 11 is a schematic block flow diagram of a system operated, according to an embodiment.

FIG. 11 illustrates a MDRC system 1100 that includes an engine 1102, patient database 1103, a clinician application 1104 that can be accessed at a clinician electronic device 1106 (e.g., gateway) for local users 1108 (e.g., clinicians), an RC application 1110 at a remote electronic device 1116 (e.g., gateway) for RC users 1112 (e.g., clinical support representatives), and at least one medical device 1114. By providing the MDRC system 1100, communication sessions can be provided.

The engine 1102 can include one or more processors for executing instructions to perform processes and methods described herein. The engine 1102 can also include a memory or storage device for storing information, including patient information, medical device information, treatment information, etc. In an example, the engine 1102 is within a cloud environment that can be accessed by numerous electronic devices other than the clinician electronic device 1106 and the remote electronic device 1116. In one example, the engine 1102 is coupled to the patient database 1103 that includes patient information, clinician information, field representative information, clinical support information, medical device information, electronic device information, including electronic device information related to the clinician electronic device 1106 and the remote electronic device 1116, or the like. The information stored can be related to an individual patient, numerous patients, patient medical devices, generic medical devices, studies, tests, other patient information, etc. In all, the patient database 1103 and engine 1102 can be coupled within a network, including a mesh network, cloud network, Bluetooth network, etc. and communicate with plural clinician electronic devices, plural remote electronic devices, etc. to obtain information related to plural patients, medical devices, treatments, or the like. In this manner, the patient database can include algorithms, including artificial intelligence algorithms for analyzing information obtained from the plural patients, medical devices, treatments, etc. to provide recommendations, modifications, updates, changes, or the like to medical devices, treatments, etc. accordingly.

The clinician electronic device 1106 is the electronic device that is at location of the patient, and/or medical device 1114. The clinician electronic device 1106 is considered local because the patient, and/or medical device 1114 is at the location of the clinician electronic device 1106 and is not remote from the patient and/or medical device 1114. In one example the medical device 1114 is an IMD. In another example, the medical device may be a neurostimulation device, monitor, or the like. The clinician electronic device can be a laptop computer, desktop computer, mobile device, server, iPad, or the like.

The clinician electronic device 1106 can include one or more processors for executing instructions to perform processes and methods described herein. The clinician electronic device can also include a memory or storage device for storing information, including patient information, medical device information, treatment information, etc. The clinician electronic device can also include an interface so that a local user 1108, such as a clinician, can input information into the clinician electronic device 1106. The interface in one example is an input device that can include a touch screen, keyboard, mouse, microphone, or the like to provide information, commands, etc. to the clinician electronic device 1106. In addition, the clinician electronic device 1106 can include an output device, such as a screen, display, speakers, etc. for providing information and data to the local user 1108. The clinician electronic device 1106 can thus be utilized by the local user 1108 to obtain information directly from the medical device 1114, and/or a patient that has the medical device 1114.

When a local user turns on the clinician electronic device 1106, the clinician electronic device 1106 detects network connectivity and automatically performs an analysis to ensure the engine 1102 is operational. In addition, the analysis can determine the identification, name, serial number, etc. associated with the clinician electronic device 1106, the version of the software, firmware, or the like of the clinician application 1104, operating system, etc. of the clinician electronic device 1106, the location or region of the clinician electronic device 1106, or the like.

In addition, the remote electronic device 1116 is located remotely, or away from the patient and/or medical device 1114. The remote electronic device 1116 can be in a hospital, clinician's office, clinician's home, or the like that is not in the location of the patient and/or medical device 1114. The remote electronic device 1116 can be a laptop computer, desktop computer, mobile device, server, iPad, or the like that includes an interface so that a RC user 1108, such as a clinician support representative, can input information into the remote electronic device 1116. The remote electronic device 1116 in one example is an electronic device of a network.

The remote electronic device 1116 can include one or more processors and a memory for executing instructions and storing information like the clinician electronic device 1106 and engine 1102. In addition, the remote electronic device 1116, like the clinician electronic device 1106, can include an interface that is an input device, along with an output device. The remote electronic device 1116 also includes the RC application 1110 that includes program instructions for obtaining patient information from the patient database 1103 via the engine 1102. The RC applicant 1110 can also communicate with the clinician application 1104 to obtain physiological information related to a patient that is obtained from the medical device 1114 via the engine 1102.

When a RC user 1108 turns on the remote electronic device 1116, the remote electronic device 1116 detects network connectivity and automatically performs an analysis to ensure the engine 1102 is operational. In addition, the analysis can determine the identification, name, serial number, etc. associated with the remote electronic device 1116, the version of the software, firmware, or the like of the RC application 1110, operating system, etc. of the remote electronic device 1116, the location or region of the remote electronic device 1116, or the like.

Figure 12:
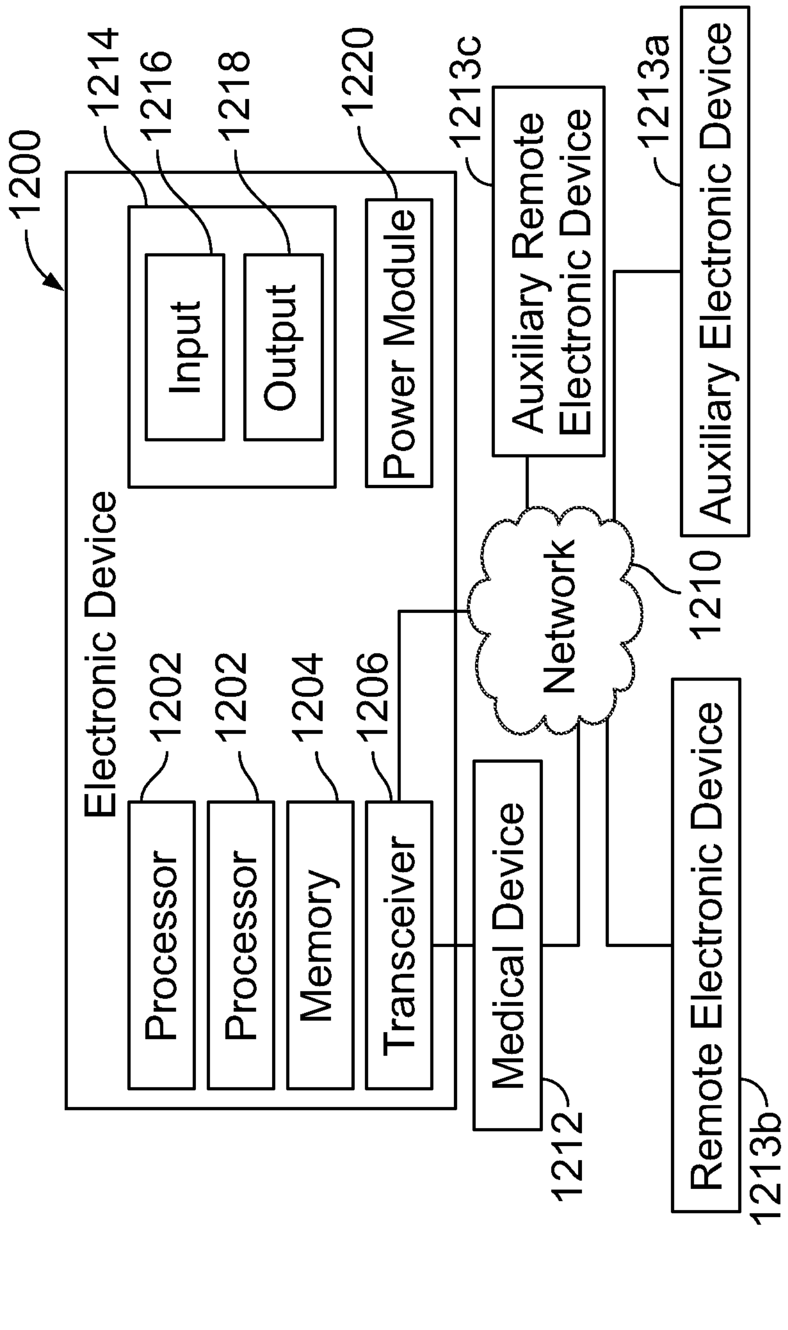
FIG. 12 is a schematic block diagram of an electronic device, according to an embodiment.

FIG. 12 illustrates a schematic block diagram of an electronic device 1200. In one example the electronic device 1200 is the clinician electronic device of FIG. 11, whereas in another example the electronic device 1200 can be the remote electronic device of FIG. 11. The electronic device 1200 can be a laptop computer, desktop computer, mobile device, server, iPad, or the like. The electronic device 1200 can include one or more processors 1202, a storage device or memory 1204, and a transceiver 1206. The transceiver 1206 is configured to communicate with other electronic devices through a network 1210. To this end, the transceiver can communicate with a server, engine, or the like, located in the cloud, over Bluetooth, etc. In addition, the transceiver can communicate with a medical device 1212. The transceiver can communicate with the medical device 1212 remotely through the network 1210, or directly. In another example, the transceiver 1206 can communicate with an auxiliary electronic device 1213*a*, a remote electronic device 1213*b*, or a remote auxiliary electronic device 1213*c*. In example embodiments, the auxiliary electronic device 1213*a* can be a smartphone, Ipad, or the like that can receive short message service (SMS) messages, such as text messages over the network. The remote auxiliary electronic device 1213*c* similarly can be a smartphone, Ipad, or the like that can also receive SMS messages. In this manner, the system can receive identification information from a clinician, clinician support representative, etc. and an SMS message can be provided by the system to the auxiliary electronic device 1213*a* and/or 1213*c* to provide verification that the clinician, or clinician support representative indeed provided the identification information. The identification information can be a username, password, login, or the like. By using a communication signal between the auxiliary electronic device 1213*a* and remote auxiliary device 1213*c*, additional security is provided.

The electronic device 1200 can also include an interface 1214 that can include an input 1216 such as a touchscreen, keyboard, mouse, microphone, etc. The electronic device 1200 can also include an output 1218 that can also include a touchscreen, display, speakers, etc. To this end, the input 1216 and output 1218 can include the same interface, display, etc. The electronic device 1200 also includes a power module 1220 for powering the electronic device 1200.

Figure 13:
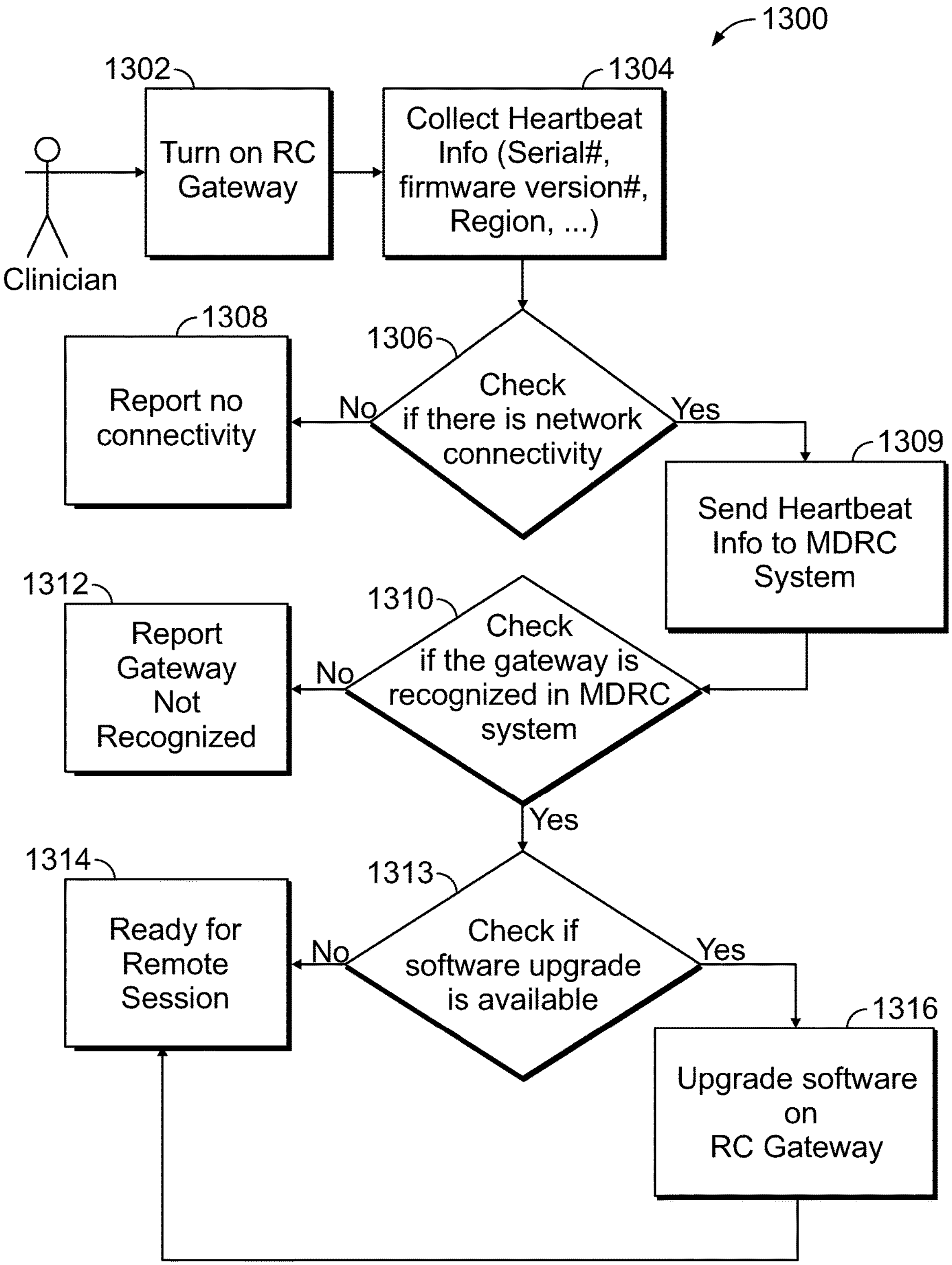
FIG. 13 is a schematic block flow diagram of a method of forming a communication session, according to an embodiment.

FIG. 13 illustrates a schematic block flow diagram of a method 1300 of forming a communication session between a clinician electronic device and a remote electronic device. In one example, the clinician electronic device includes a clinician application that is configured to receive information from a medical device, including an IMD. In another example, the remote electronic device includes an RC application configured to provide instructions for communicating with the clinician electronic device and an engine that is coupled to a patient database. In example embodiments, the MDRC system of FIG. 11 implements the method of FIG. 13, where the clinician electronic device, remote electronic device, or engine, each can include one or more processors configured to execute instructions to accomplish the method or a portion of the method.

At 1302, the clinician electronic device is activated. To activate the clinician electronic device a power source can be turned on, a screen saver exited, a login entered, or the like. At 1304, the one or more processors of the clinician electronic device obtain clinician electronic device information. Clinician electronic device information can include identification information including serial number, device name, username, etc.; software information including software version, available software updates, or the like; firmware information, including firmware version, firmware updates, etc.; location information, including global positioning information, network location information, electronic device location information, or the like; etc. In one example, the clinician electronic device information is considered heartbeat information related to the clinician electronic device.

At 1306, the one or more processors determine if network connectivity is available. After obtaining the clinician electronic device information, determination made whether a communication session can be set up between the clinician electronic device and the remote electronic device via the engine. To accomplish, a network for communication must be available. If a network is not available, at 1308 the one or more processers alert the local user that network connectivity is not available, and the method ends. Until network connectivity is available, the remote electronic device cannot perform the method and processes herein.

If at 1306 network connectivity is available, then at 1309 the heartbeat information such as identification information including serial number, device name, username, etc.; software information including software version, available software updates, or the like; firmware information, including firmware version, firmware updates, etc.; location information, including global positioning information, network location information, electronic device location information, or the like; etc. is communicated to the engine of the MDRC system.

Then, at 1310, the one or more processors check to see if the pathway is recognized by the engine. For example, a determination can be made whether the clinician electronic device is registered for communication with the engine. To ensure safety and confidentiality of patient information, a registration process can be undertaken. In one example, the registration process includes authentication that the local user is a clinician authorized to access the engine. The authentication in examples can be provided with a login, bio-scanning such as fingerprint, retina scanning, facial recognition, etc., security questions, via use keys, one-time dependent password, or the like. If at 1310 the user of the clinician electronic device is not registered, then at 1312 the one or more processors sends the user of the clinician electronic device to a registration process. The registration process in one example can be a webpage, portal, or the like where information related to the user may be provided, and authentication information can be provided for later use.

If at 1310 the user is registered, or if the user becomes registered at 1312, then at 1313, a determination is made whether a software upgrade is available. If a software upgrade is not available, then 1314 the one or more processors form a communication session with the engine and provide the clinician electronic device information to the engine. By providing the obtained clinician electronic device information, that includes clinician information, patient information, patient treatment information, medical device information, or the like, the engine can begin analyzing the information, saving the information, or the like to enhance and improve treatment for the patient.

If at 1313 a software upgrade is available, then at 1316 the software is upgraded. In this manner, a software upgrade can be provided any time the engine is accessed. Then, after the upgrade, the communication session can begin.

Figure 14A:
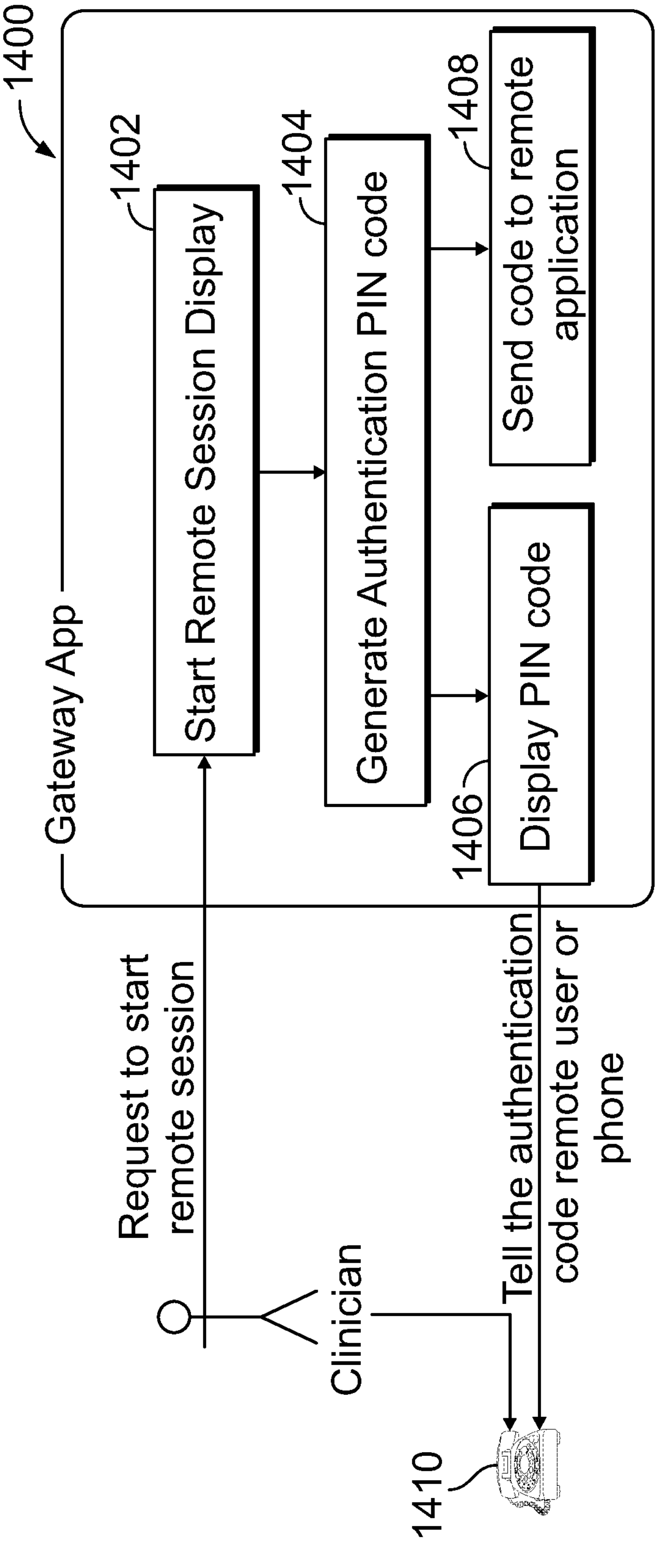
FIG. 14*a* is a schematic block flow diagram of a process of starting a communication session, according to an embodiment.

FIG. 14*a* illustrates a flow block diagram of a process 1400 of a clinician electronic device starting a communication session with a remote electronic device. In one example, the clinician electronic device and remote electronic device are clinician electronic device and remote electronic device previously described.

At 1402, one or more processors of a clinician electronic device receive an instruction from a clinician to start a new communication session with a clinician application that is on the clinician electronic device. In one example, the clinician application is a software application that is downloaded or uploaded onto the clinician electronic device. The clinician application can include clinician information, patient information, medical device information, treatment information, or the like to assist in providing a treatment to a local patient. During the startup process, the one or more processors can check to see if network connectivity is provided. If not, a report can be provided to the clinician application that can be communicated to the clinician that no connectivity is provided. In one example, a message on a popup is presented on an output, such as a display that can be read by the clinician.

If connectivity is provided, a determination can be made whether the clinician electronic device is registered to utilize the engine. To ensure that information related to the medical device, patient, clinician, etc. are not being obtained by a nefarious individual, a registration process is provided to ensure only qualified clinicians are utilizing the system. If a determination is made that the clinician is not registered, then the clinician can be directed to a registration location. The registration location can be a webpage, website, or the like where the clinician can provide information about themselves, and/or a patient, so that verification can occur that the clinician is who they say they are, and to ensure the clinician is qualified to receive patient information. In another example, the one or more processors can provide a website address, phone number, or the like that can be utilized by a clinician to register themselves in the system.

At 1404, one or more processors of the MDRC system generates an authentication code in response to the request to start a remote session. In one example, the authentication code can be a personal identification number (PIN), a random number, a one-time time restricted password, public key, or the like.

At 1406, one of more processors of the MDRC system displays the authentication code for review by the clinician. At the same time, at 1408, the authentication code is communicated to the RC application for a remote electronic device.

Figure 14B:
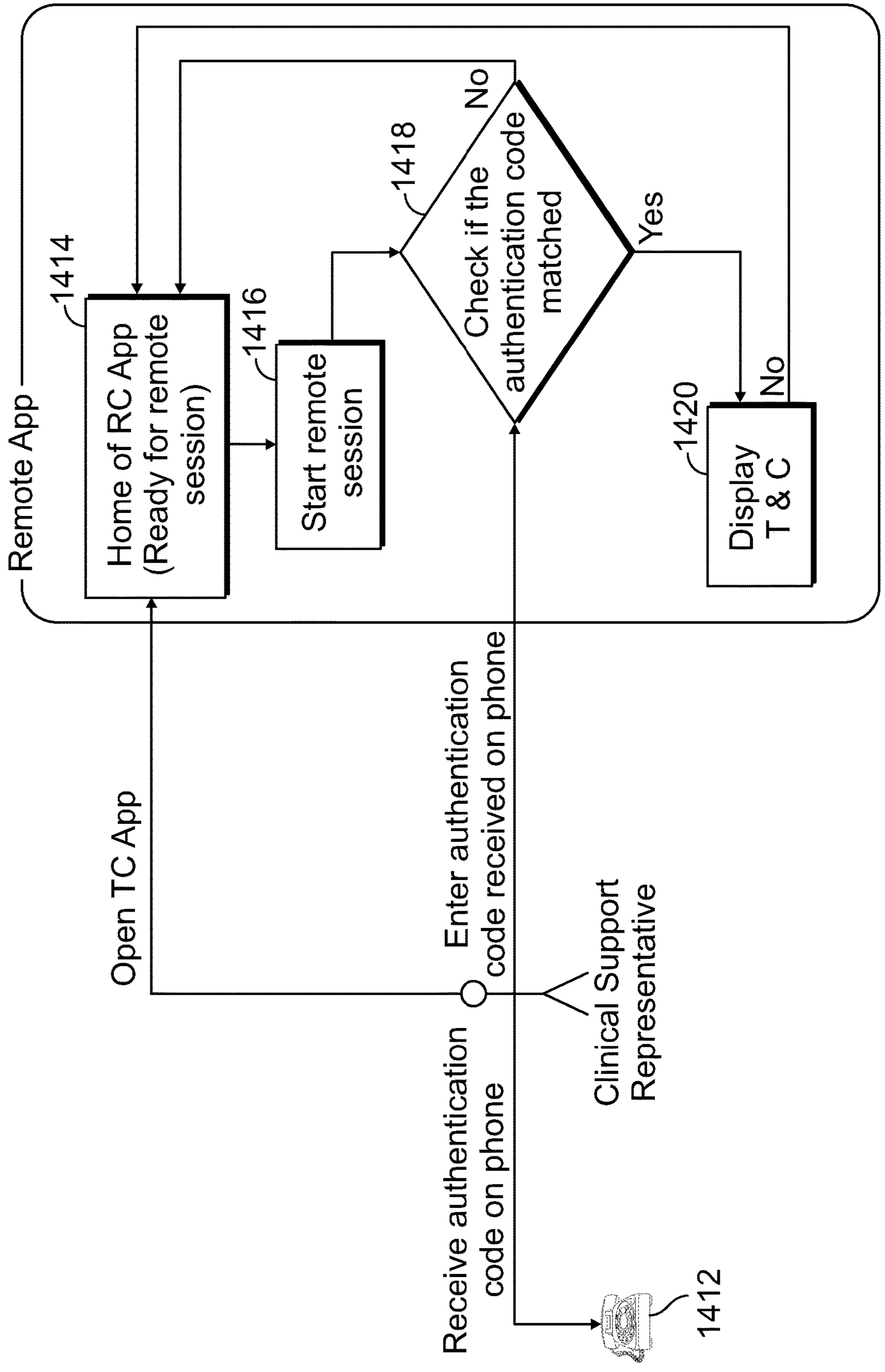
FIG. 14*b* is a schematic block flow diagram of a process of starting a communication session, according to an embodiment.

Once the clinician sees the authentication code on the display, the clinician can communicate the authentication code via an auxiliary electronic device 1410 to a remote auxiliary electronic device 1412 (See FIG. 14*b*). In one example, the clinician can communicate a SMS message from a smartphone to a smartphone of a RC user. In particular, the RC user may have a remote auxiliary electronic device such as a smartphone, iPad, or the like. By using the SMS message to that remote auxiliary electronic device, an extra level of security is provided as a result of the communication being outside of the MDRC system.

FIG. 14*b* illustrates a schematic block diagram of how the RC application is utilized so that a RC user (e.g., clinician support representative) enters a remote communication session. When the RC user receives the authentication code at the remote auxiliary electronic device 1412, the RC user can start up the clinician application.

The clinician application at 1414 is ready to begin a remote session at any time. In this manner, the RC user can open the clinician application and enter the authentication code to start the session at 1416. Once the authentication code is inputted into the remote electronic device, a determination is made at 1418, whether the authentication code is accurate, or matches the authentication code provided to on the display to the clinician.

If the authentication code is incorrect, then the RC application provides a home page that the remote session is ready, and no communication session is provided. However, if at 1418 RC application authenticates the authentication code, then at 1420 terms and conditions are provided displayed on a display to the RC user. If the terms and conditions are not accepted, the RC application provides the home page that the remote session is ready. If the terms and conditions are accepted, then the remote session begins.

Figure 14C:
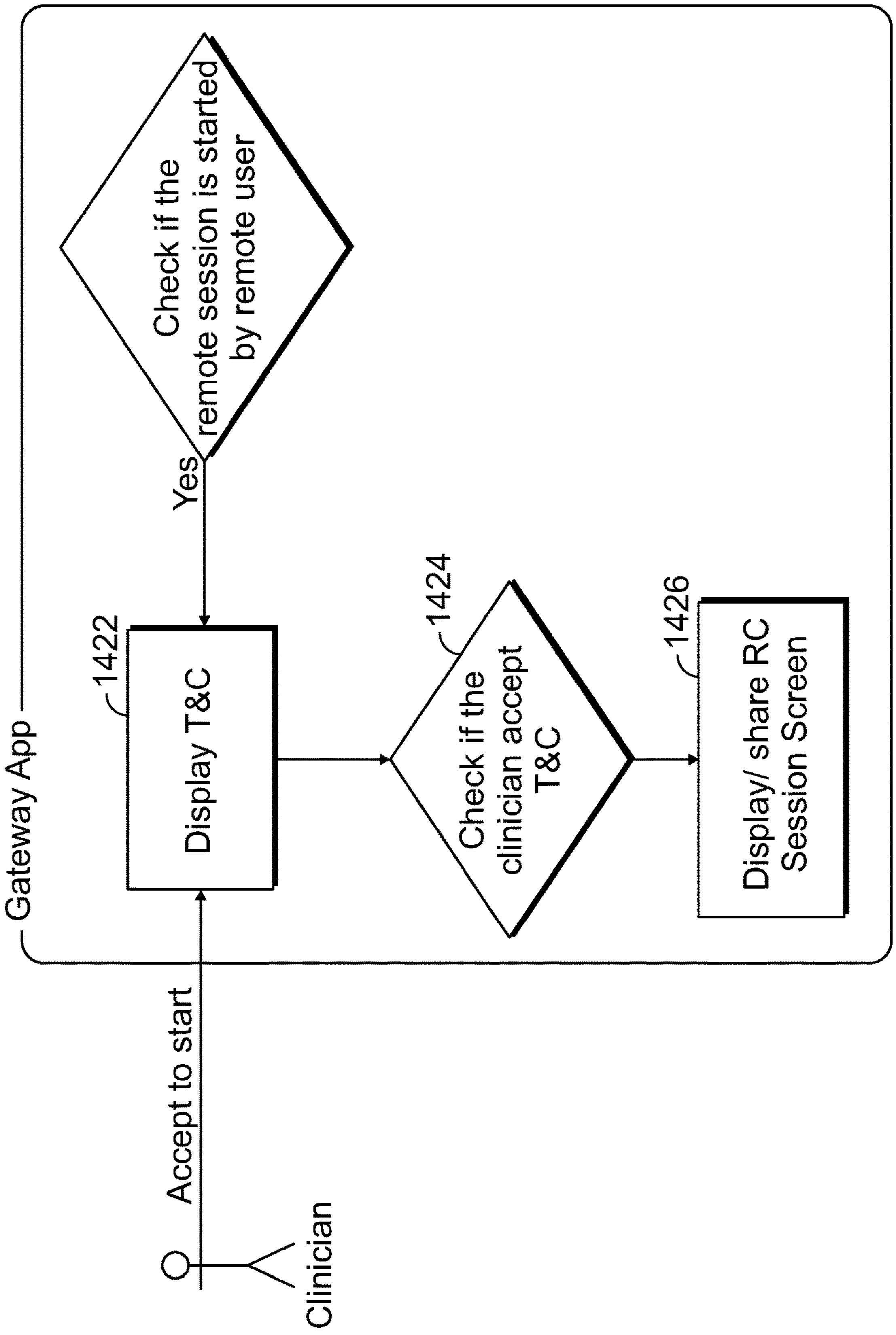
FIG. 14*c* is a schematic block flow diagram of a process of starting a communication session, according to an embodiment.

FIG. 14*c* illustrates what occurs at the clinician application once the remote session is accepted by the RC user at 1420 by the RC user accepting the terms and conditions. At 1422, the one or more processes of the clinician electronic device display on a display terms and conditions for the clinician to accept. Then at 1424, the one or more processors of the clinician electronic device determine if the clinician has accepted the terms and conditions. If not, a homepage is provided, and the remote session does not occur. However, if the terms and conditions are accepted, then at 1426, the remote session is started for the clinician application.

Figure 14D:
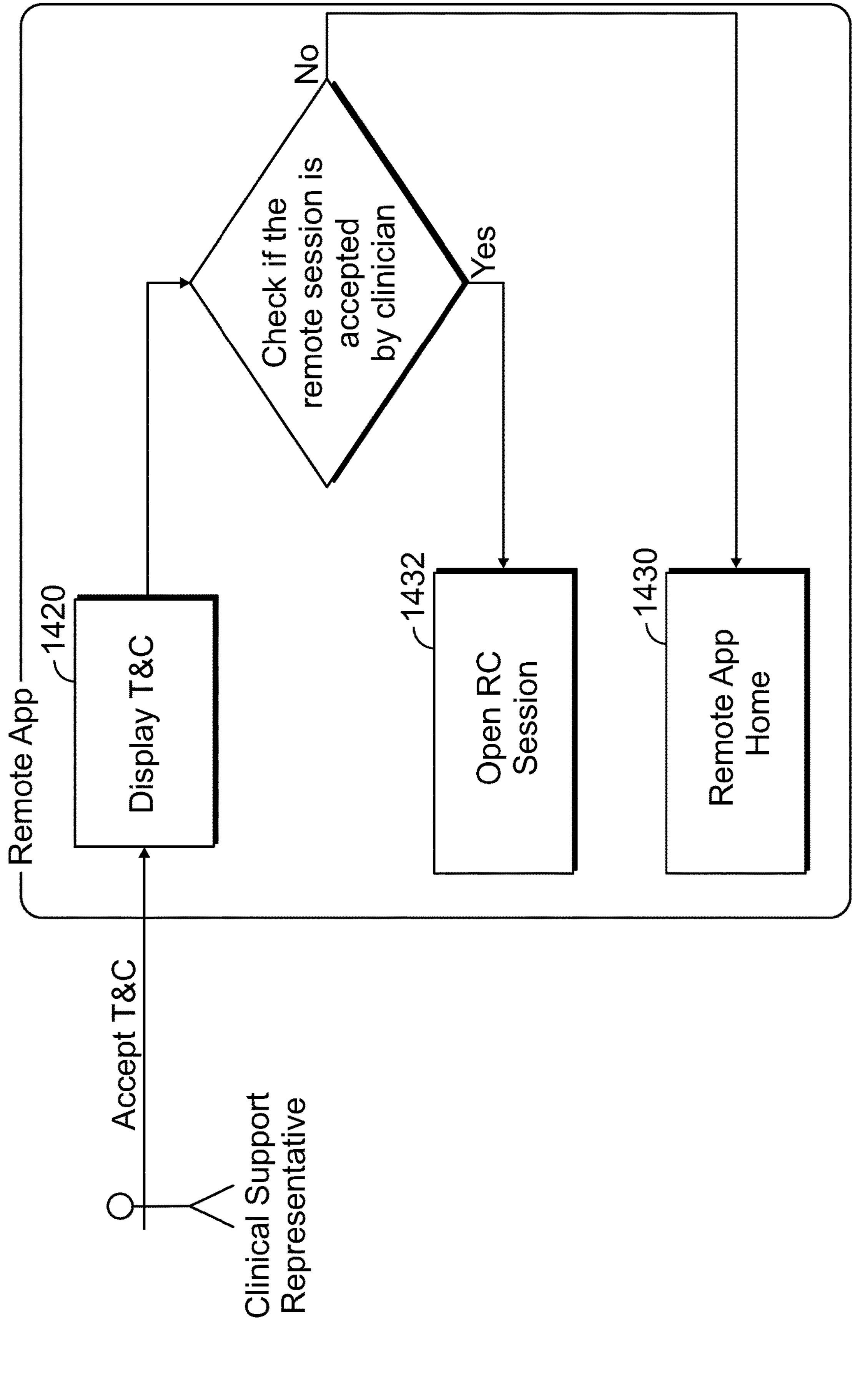
FIG. 14*d* is a schematic block flow diagram of a process of starting a communication session, according to an embodiment.

FIG. 14*d* illustrates what occurs at the RC application after the terms and conditions are accepted by the RC user at 1420. In response to the terms and conditions being accepted, a determination is made at 1428 whether the clinician has accepted the remote session as a result of accepting the terms and conditions. If the terms and conditions are not accepted by the clinician, then at 1430, the home page is displayed, and no remote session occurs. If, however, the clinician accepts the terms and conditions, then at 1432, the remote session is started for the RC application.

Figure 15A:
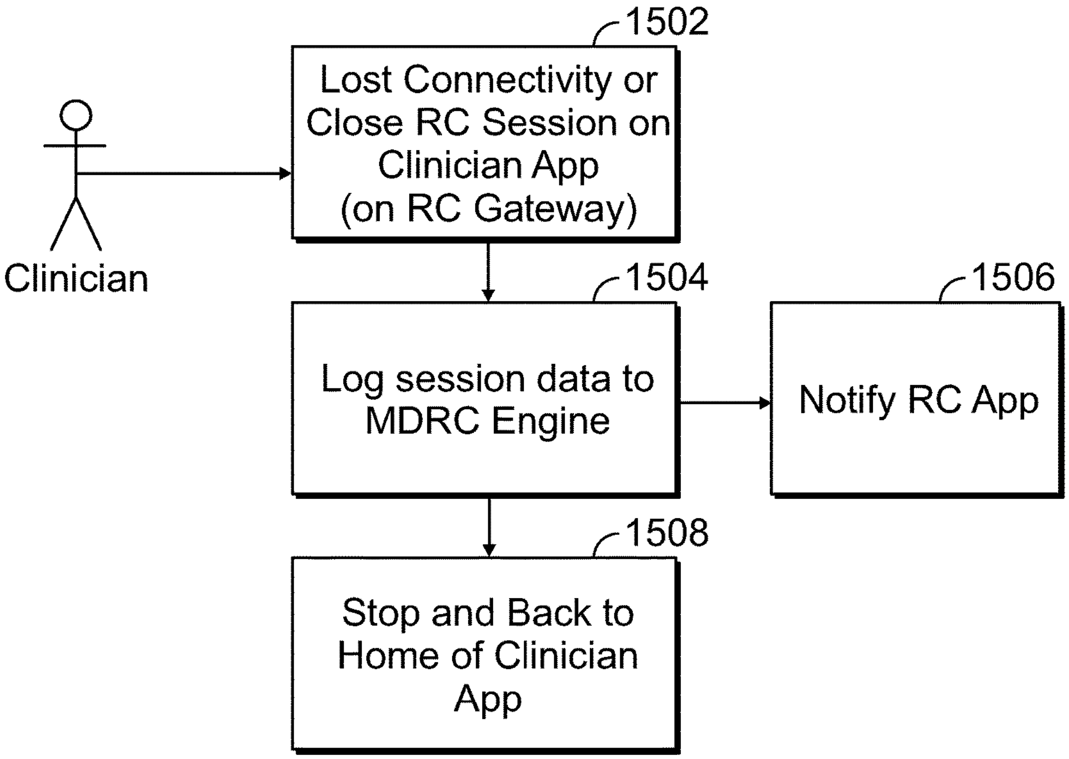
FIG. 15*a* is a schematic block flow diagram of a process of terminating a communication session, according to an embodiment.
Figure 15B:
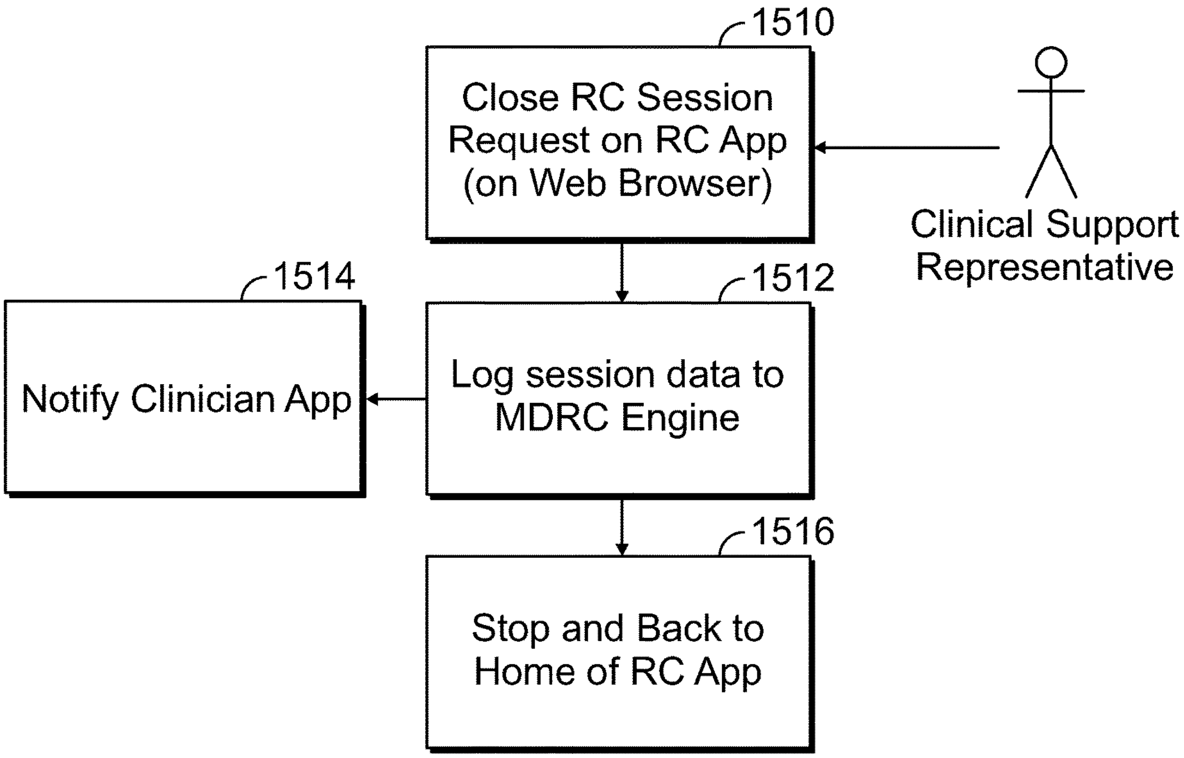
FIG. 15*b* is a schematic block flow diagram of a process of terminating a communication session, according to an embodiment.
Figure 15C:
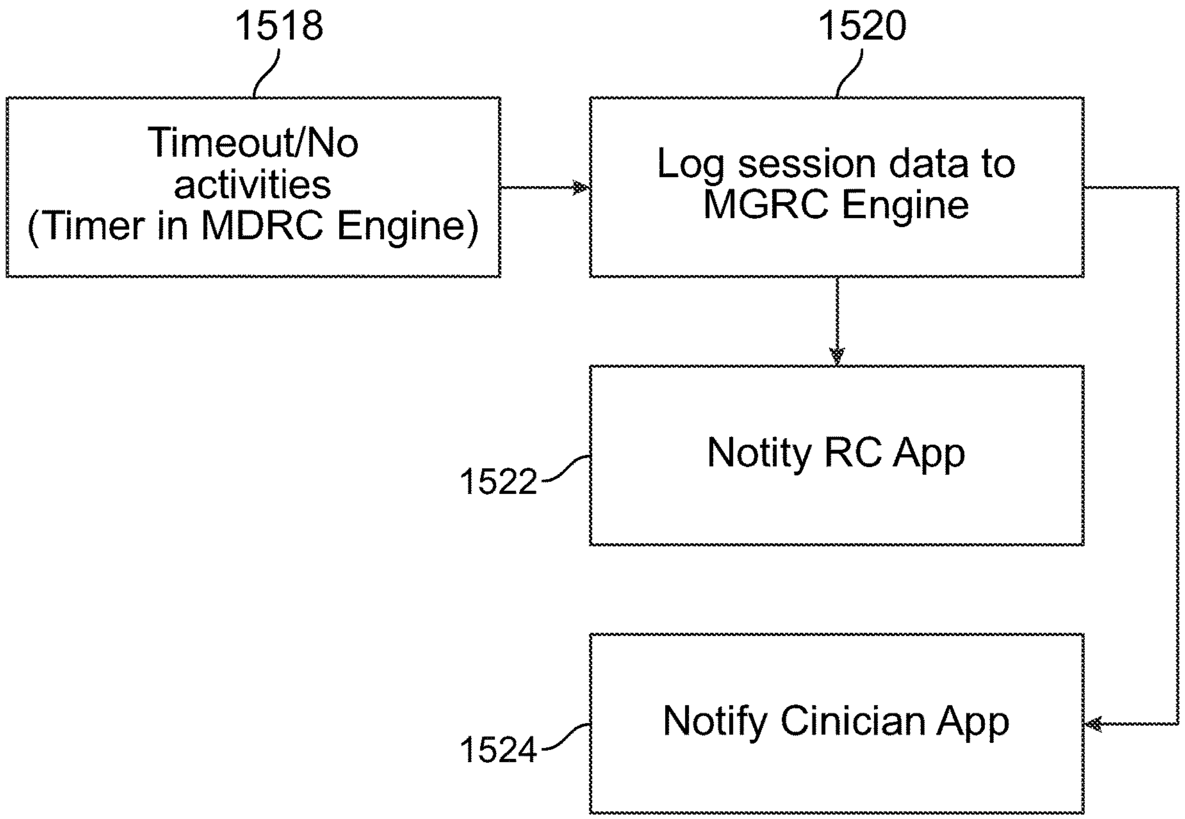
FIG. 15*c* is a schematic block flow diagram of a process of terminating a communication session, according to an embodiment.

FIGS. 15*a*-15*c* illustrate block flow diagrams of processes and methods that can occur during a communication session that results in termination of the communication session. FIG. 15*a*, illustrates what occurs when at 1502 connectivity is lost, or when the communication session is closed by the clinician application. In response to either the loss of connectivity, or the closing of the clinician application, at 1504, one or more processors at the engine log session data to the engine. By saving the log session data automatically, no information is lost as a result of an unintended stopping of the communication session. In addition, at 1506, once the information is logged, a communication is sent to the RC application that the communication session has ended as a result of a loss in connectivity, or as a result of the clinician electronic device terminating the session. In this manner, the RC application can provide instructions to display, or otherwise communicate the ending of the communication session to the RC user. Further, at 1508, the clinician application terminates the communication session, and provides instructions to display or present a home screen to the local user (clinician).

FIG. 15*b* illustrates a schematic flow block diagram of the process that occurs when the RC user (e.g., clinical support representative) terminates the communication session. At 1510, the RC user provides an input to close the communication session at the RC application. In response to receiving the input, at 1512, the RC application communicates with the engine, and all session data is logged, or saved, at the engine. Then at 1514 a communication is provided to the clinician application to notify the local user (clinician) that the communication session has been terminated by the RC user. At 1516, the RC application provides the home screen for the RC user.

FIG. 15*c* illustrates a schematic flow block diagram of the process that occurs when the communication session ends as a result of inactivity. When the communication session begins, the engine monitors the communication between the RC application and the clinician application. A timer is provided that is set at a determined amount of time for no communication to occur. In one example, the determined amount of time is five minutes, in another example, the determined amount of time is ten minutes, an hour, two hours, etc. If an error occurs, by providing a timer, the communication session can end, preventing another from coming across an open communication session. So, at 1518, the engine determines that a threshold time (e.g., the determined amount of time) has been exceeded, and in response, the communication session is terminated. At 1520, the session data is logged and saved by the engine. At 1522 the RC application is notified, and at 1524 the clinician application is also notified. In this manner, each application can provide information at an interface that the communication session has ended, and a home screen can be provided.

Closing

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method, or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random-access memory (RAM), a dynamic random-access memory (DRAM), a read-only memory (ROM), an erasable programmable read-only memory (EPROM or Flash memory), a portable compact disc read-only memory (CD- ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices, and program products according to various example embodiments. The program instructions may be provided to a processor of a general-purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A medical device assembly comprising:

a clinician programming device configured to communicate with an implanted medical device of a patient;

the clinician programming device including one or more processors configured to:

communicate initial program instructions to a remote programming engine, the remote programming engine comprising one or more processors configured to:

simulate operation of the implanted medical device based on the initial program instructions; and communicate updated program instructions to the implanted medical device based on the operation simulated.

2. The medical device assembly of claim 1, wherein to simulate operation of the implanted medical device, the one or more processors of the remote programming engine are further configured to determine initialization of a programming session, whether the programming session is pending, and termination of the programming session.

3. The medical device assembly of claim 2, wherein the one or more processors of the remote programming engine are further configured to:

determine whether the termination of the programming session is in response to completion of the programming session, or in response to a programming error.

4. The medical device assembly of claim 2, wherein to determine initialization of the programming session, the one or more processors of the remote programming engine are further configured to:

generate an asynchronous remote programming profile that includes the updated program instructions; and communicate the asynchronous remote programming profile to the implanted medical device.

5. The medical device assembly of claim 4, wherein the one or more processors of the clinician processing device are further configured to:

generate and display a pending message in response to communication of the asynchronous remote programming profile; and present the pending message until an acknowledgment message is received from a patient application.

6. The medical device assembly of claim 5, wherein the one or more processors of the clinician processing device are further configured to:

display a success message in response to receiving the acknowledgment message.

7. The medical device assembly of claim 5, the one or more processors of the remote programming engine are further configured to:

start a timer in response to communicating the asynchronous remote programming profile; and communicate a failure message in response to the timer reaching a determined period before receiving the acknowledgment message.

8. A medical device assembly comprising:

a clinician device configured to communicate with an implanted medical device of a patient;

the clinician programming device including one or more processors configured to:

communicate initial program instructions related to a programming session of the implanted medical device;

receive updated program instructions from a remote programming engine based on a simulation of operation of the implanted medical device based on the initial program instructions; and communicate updated program instructions to the implanted medical device based on the simulation.

9. The medical device assembly of claim 8, wherein the one or more processors are configured to receive communication related to initialization of the implantable medical device, related to whether the programming session is pending, and related to termination of the programming session.

10. The medical device assembly of claim 9, wherein the one or more processors are further configured to:

determine whether the termination of the programming session is in response to completion of the programming session, or in response to a programming error.

11. The medical device assembly of claim 9, the one or more processors are further configured to:

receive a message from a virtual device engine (VDE), the message including the updated program instructions for the programming session that is related to a treatment to be performed by the implanted medical device;

receive an asynchronous remote programming profile from the VDE that includes the updated program instructions; and communicate the asynchronous remote programming profile to the implanted medical device.

12. The of medical device assembly of claim 11, the one or more processors further configured to:

generate and display a pending message in response to communicating the asynchronous remote programming profile; and present the pending message until an acknowledgment message is received from a patient application.

13. The medical device assembly of claim 12, the one or more processors further configured to:

display a success message in response to receiving the acknowledgment message.

14. The medical device assembly of claim 12, the one or more processors further configured to:

display a failure message in response to a timer reaching a determined period before receiving the acknowledgment message.

* * * * *